(12) United States Patent
Kato et al.

(10) Patent No.: US 9,679,189 B2
(45) Date of Patent: Jun. 13, 2017

(54) ELAPSED-TIME DETERMINATION APPARATUS, DECIDING APPARATUS, DECIDING METHOD, AND NON-TRANSITORY COMPUTER-READABLE RECORDING MEDIUM STORING CONTROL PROGRAM

(71) Applicant: Panasonic Corporation, Osaka (JP)

(72) Inventors: Yumiko Kato, Osaka (JP); Yumi Wakita, Nara (JP); Jun Ozawa, Nara (JP); Naoshi Kondo, Kyoto (JP); Yuichi Ogawa, Kyoto (JP); Tetsuhito Suzuki, Kyoto (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 14/859,246

(22) Filed: Sep. 18, 2015

(65) Prior Publication Data
US 2016/0092723 A1     Mar. 31, 2016

(30) Foreign Application Priority Data

Sep. 26, 2014 (JP) .................. 2014-197554
Apr. 14, 2015 (JP) .................. 2015-082841

(51) Int. Cl.
    *G06K 9/00*         (2006.01)
    *G01B 11/24*      (2006.01)
    (Continued)

(52) U.S. Cl.
    CPC .......... *G06K 9/00147* (2013.01); *G01B 11/24* (2013.01); *G01N 33/12* (2013.01);
    (Continued)

(58) Field of Classification Search
    CPC .......... G06K 9/00147; G06K 9/00134; G06K 9/2036; G06T 7/001
    See application file for complete search history.

(56) References Cited

U.S. PATENT DOCUMENTS 9,316,595 B2 *    4/2016    Wakita .................. G01N 21/84
2005/0074834 A1 *   4/2005    Chaplen ............. G01N 15/1475
                                                                                                          435/34
(Continued)

FOREIGN PATENT DOCUMENTS

| EP | 2189789 | 5/2010 |
|---|---|---|
| JP | 2002-360223 | 12/2002 |
| JP | 2008-111823 | 5/2008 |

OTHER PUBLICATIONS

Masatoshi Okutomi, "Digital Image Processing", CG-ARTS, Jul. 2014, pp. 177-184, pp. 220-223.

*Primary Examiner* — Gregory M Desire
(74) *Attorney, Agent, or Firm* — Wenderoth, Lind & Ponack, L.L.P.

(57) ABSTRACT

An elapsed-time determination apparatus includes: a storage unit that stores correlation information indicating a correlation between a state of a melanophore of a fish and an amount of time elapsed since the death of the fish; an acquisition unit that acquires an image of a fish; an analysis unit that detects a state of a melanophore of a fish by analyzing an image acquired by the acquisition unit; and a determination unit that determines the amount of time elapsed since the death of the fish in accordance with the state of the melanophore of the fish detected by the analysis unit, based on the correlation information, and outputs determination results.

9 Claims, 27 Drawing Sheets

(51) Int. Cl.
*G01N 33/12* (2006.01)
*G06K 9/20* (2006.01)
*G06T 7/00* (2017.01)
*G06T 7/62* (2017.01)
*G06T 7/64* (2017.01)
G04F 13/02 (2006.01)

(52) U.S. Cl.
CPC ....... *G06K 9/00134* (2013.01); *G06K 9/2036* (2013.01); *G06T 7/0004* (2013.01); *G06T 7/62* (2017.01); *G06T 7/64* (2017.01); *G04F 13/02* (2013.01); *G06T 2207/30128* (2013.01)

(56) References Cited

U.S. PATENT DOCUMENTS

| | | | |
|---|---|---|---|
| 2006/0115895 A1* | 6/2006 | Goldsmith | A01K 67/0275 435/325 |
| 2009/0010849 A1* | 1/2009 | McGrath | A61K 49/0008 424/9.2 |
| 2010/0119119 A1* | 5/2010 | Rittscher | G01N 33/5088 382/110 |
| 2012/0210449 A1* | 8/2012 | Huang | A01K 67/027 800/3 |
| 2016/0092723 A1* | 3/2016 | Kato | G06K 9/00147 382/110 |

* cited by examiner

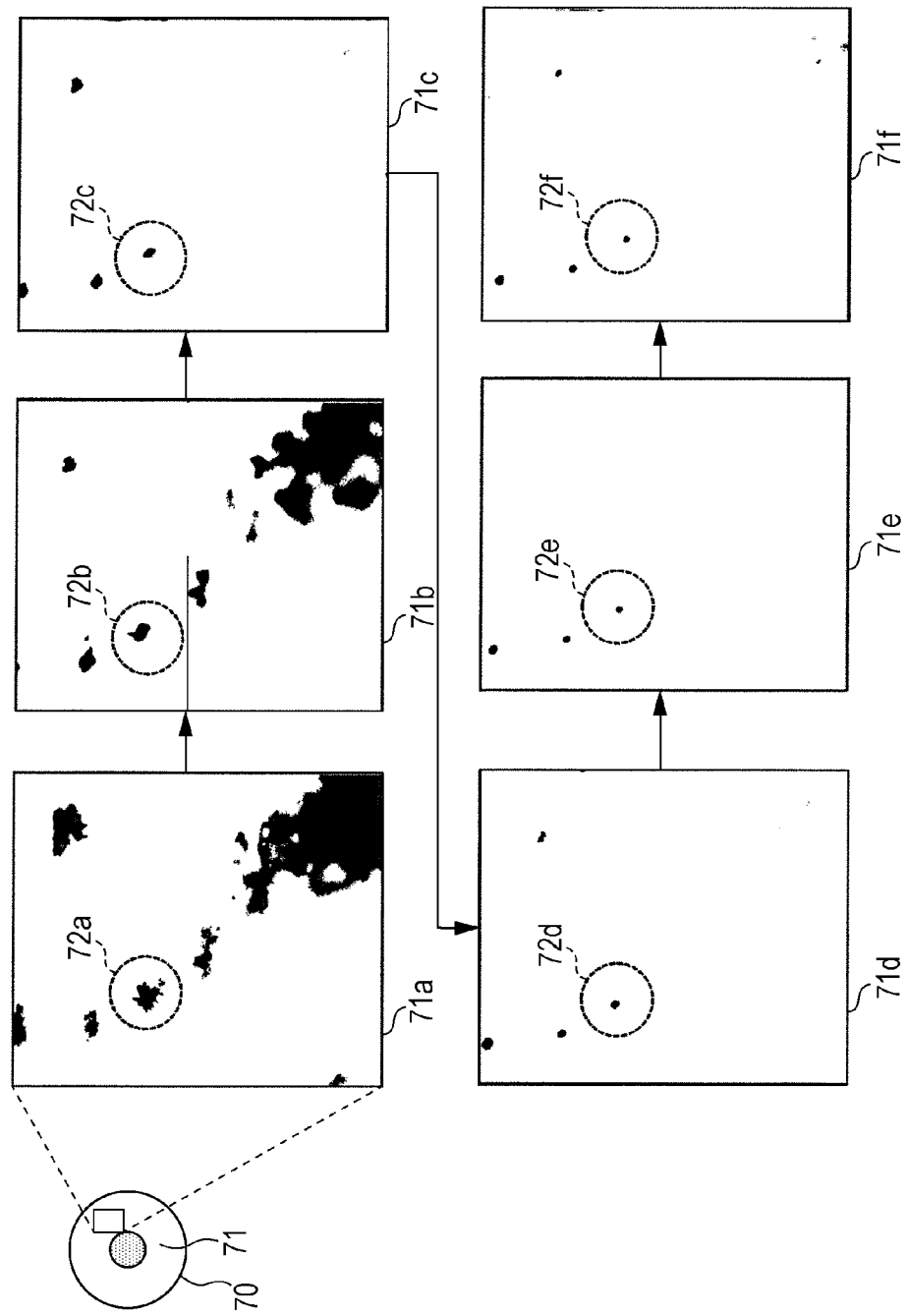

| AVERAGE AREA ($\mu m^2$) | TIME ELAPSED (HOURS) |
|---|---|
| ≥ 1,000,000 | < 4 |
| ≥ 100,000, < 1,000,000 | ≥ 4, < 5 |
| ≥ 50,000, < 100,000 | ≥ 5, < 6 |
| ≥ 10,000, < 50,000 | ≥ 6, < 8 |
| ⋮ | ⋮ |

| COMPLEXITY (PERIMETER/CIRCUMFERENCE) | TIME ELAPSED (HOURS) |
|---|---|
| ≥3 | <4 |
| ≥2, <3 | ≥4, <5 |
| ≥1.5, <2 | ≥5, <6 |
| ≥1.2, <1.5 | ≥6, <8 |
| ⋮ | ⋮ |

| TIME CLASS | TIME ELAPSED | FEATURES | | | |
|---|---|---|---|---|---|
| | | ROUNDNESS | BOUNDING BOX | AREA | PERIMETER |
| 1 | 3 | 0.1 | 158×170 | 10744 | 3280 |
| 2 | 4 | 0.13 | 136×159 | 9730 | 2537 |
| 3 | 5 | 0.2 | 102×115 | 7038 | 1302 |
| ⋮ | ⋮ | ⋮ | ⋮ | ⋮ | ⋮ |

FIG. 24

CORRELATION INFORMATION A

| AVERAGE AREA (μm²) | TIME ELAPSED (HOURS) |
|---|---|
| ≥ 1,000,000 | < 4 |
| ≥ 100,000, < 1,000,000 | ≥ 4, < 5 |
| ≥ 50,000, < 100,000 | ≥ 5, < 6 |
| ≥ 10,000, < 50,000 | ≥ 6, < 8 |
| ⋮ | ⋮ |

CORRELATION INFORMATION B

| AVERAGE AREA (μm²) | TIME ELAPSED (HOURS) |
|---|---|
| ≥ 1,000,000 | < 8 |
| ≥ 100,000, < 1,000,000 | ≥ 8, < 12 |
| ≥ 50,000, < 100,000 | ≥ 12, < 16 |
| ≥ 10,000, < 50,000 | ≥ 16, < 18 |
| ⋮ | ⋮ |

CORRELATION INFORMATION C

| AVERAGE AREA (μm²) | TIME ELAPSED (HOURS) |
|---|---|
| ≥ 1,000,000 | < 8 |
| ≥ 100,000, < 1,000,000 | ≥ 8, < 20 |
| ≥ 50,000, < 100,000 | ≥ 20, < 30 |
| ≥ 10,000, < 50,000 | ≥ 30, < 40 |
| ⋮ | ⋮ |

FIG. 26

CORRELATION INFORMATION A

| COMPLEXITY (PERIMETER/CIRCUMFERENCE) | TIME ELAPSED (HOURS) |
|---|---|
| ≥3 | <4 |
| ≥2, <3 | ≥4, <5 |
| ≥1.5, <2 | ≥5, <6 |
| ≥1.2, <1.5 | ≥6, <8 |
| ⋮ | ⋮ |

CORRELATION INFORMATION B

| COMPLEXITY (PERIMETER/CIRCUMFERENCE) | TIME ELAPSED (HOURS) |
|---|---|
| ≥3 | <8 |
| ≥2, <3 | ≥8, <12 |
| ≥1.5, <2 | ≥12, <16 |
| ≥1.2, <1.5 | ≥16, <18 |
| ⋮ | ⋮ |

CORRELATION INFORMATION C

| COMPLEXITY (PERIMETER/CIRCUMFERENCE) | TIME ELAPSED (HOURS) |
|---|---|
| ≥3 | <8 |
| ≥2, <3 | ≥8, <20 |
| ≥1.5, <2 | ≥20, <30 |
| ≥1.2, <1.5 | ≥30, <40 |
| ⋮ | ⋮ |

ELAPSED-TIME DETERMINATION APPARATUS, DECIDING APPARATUS, DECIDING METHOD, AND NON-TRANSITORY COMPUTER-READABLE RECORDING MEDIUM STORING CONTROL PROGRAM

BACKGROUND

1. Technical Field

The present disclosure relates to an elapsed-time determination apparatus that determines elapsed time after death of a fish based on an image of the fish, a deciding apparatus, a deciding method, and a non-transitory computer-readable recording medium storing a control program.

2. Description of the Related Art

Japanese Patent No. 4291381 discloses a method of judging freshness of edible fish using a K value. The K value is an index of freshness that takes advantage of the fact that adenosine triphosphate (ATP) in muscle tissue of a living body breaks down after death of the organism, and further changes from inosine monophosphate to hypoxanthine. That is to say, the K value is a percentage expression of the total amount of inosine and hypoxanthine as to the total amount of adenosine triphosphate, adenosine diphosphate, adenosine monophosphate, inosine monophosphate, inosine, and hypoxanthine. Fresh fish includes large amounts of adenosine triphosphate, adenosine diphosphate, adenosine monophosphate, and inosine monophosphate. Fish which have lost freshness due to time having elapsed after death include large amounts of inosine and hypoxanthine. Accordingly, the smaller the K value is, the fresher the fish is.

EP Patent Application No. 2189789 discloses a method of determining an amount of time elapsed after death, using a boundary position between the pupil portion of the eye and the surrounding white portion by image processing based on an image of the fish. This method takes advantage of the fact that the boundary position between the pupil and the white changes over time after death.

The K value is obtained by directly measuring chemical substances contained in the flesh of fish that are deeply related to freshness, so the K value is a precise indicator of the freshness of the fish flesh. However, measurement of the chemical substances contained in the flesh of fish is conducted by extracting flesh from the fish. That is to say, obtaining a K value necessitates marring the merchandise that is the fish, meaning that obtaining the K value reduces the value of the merchandise.

Further, judgment of the freshness using the boundary position between the pupil and the white is affected by differences such as the type of the fish, for example. Accordingly, there may be cases where the boundary positions cannot be appropriately identified, and judging freshness becomes difficult.

SUMMARY

One non-limiting and exemplary embodiment provides an elapsed-time determination apparatus that determines an amount of time elapsed after death of a fish, without damaging the fish, and without depending on the boundary position between the pupil and the white.

In one general aspect, the techniques disclosed here feature an elapsed-time determination apparatus including: a storage unit that stores correlation information indicating a correlation between a state of a melanophore of a fish and an amount of time elapsed since death of the fish; an acquisition unit that acquires an image of a fish; an analysis unit that detects a state of a melanophore of a fish by analyzing the image acquired by the acquisition unit; and a determination unit that determines the amount of time elapsed since the death of the fish in accordance with the state of the melanophore of the fish detected by the analysis unit, based on the correlation information, and outputs determination results.

According to the present disclosure, an amount of time elapsed after death of a fish can be determined without damaging the fish, and without depending on the boundary position between the pupil and the white.

It should be noted that these comprehensive or specific embodiments may be implemented as a system, a method, an integrated circuit, a computer program, or a computer-readable recording medium, or any combination of a device; system, method, integrated circuit, computer program, and computer-readable recording medium. Examples of a computer-readable recording medium may include non-volatile recording media, such as a CD-ROM (Compact Disc-Read Only Memory) and so forth.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a diagram illustrating binary images of an iris of a fish;

FIG. 24 is a diagram exemplarily illustrating three sets of correlation information (tables illustrating correlation between the average area of melanophores and an amount of time elapsed after death of the fish) according the first modification of the third embodiment;

FIG. 26 is a diagram exemplarily illustrating three sets of correlation information (tables illustrating correlation between the complexity of the shape of melanophores and an amount of time elapsed after death of the fish) according the first modification of the third embodiment;

DETAILED DESCRIPTION

Figure 2A:
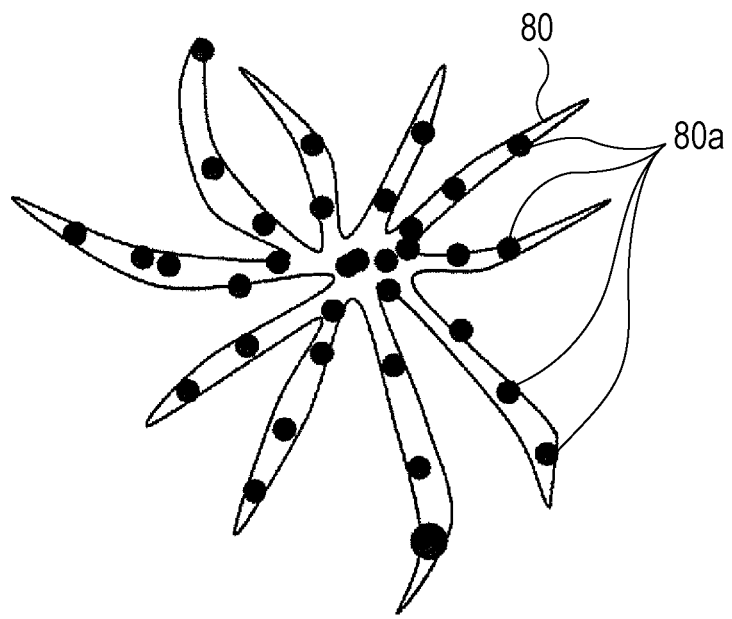
FIG. 2A is a schematic diagram illustrating a distribution state (dispersed state) of pigment granules in a melanophore.

An elapsed-time determination apparatus according to an aspect of the present disclosure includes: a storage unit that stores correlation information indicating a correlation between a state of a melanophore of a fish and an amount of time elapsed since death of the fish; an acquisition unit that acquires an image of a fish; an analysis unit that detects a state of a melanophore of a fish by analyzing the image acquired by the acquisition unit; and a determination unit that determines the amount of time elapsed since the death of the fish in accordance with the state of the melanophore of the fish detected by the analysis unit, based on the correlation information, and outputs determination results. The storage unit may store correlation information beforehand, or may acquire correlation information from outside of the elapsed-time determination apparatus. Accordingly, the image of the fish is analyzed and the amount of time elapsed since the death of the fish is determined based on the state of the melanophore, so determination can be performed without marring the fish and without depending on the boundary position between the pupil and white of the eye. The user can know the amount of time elapsed since the death of the fish simply be causing the elapsed-time determination apparatus to acquire an image of a fish by photograph or the like, for example.

The image of the fish acquired by the acquisition unit may include part of an iris or fin of the fish. Accordingly, analysis can be performed in an image suited for analysis of melanophores so determination of the amount of time elapsed since the death of the fish can be suitably performed.

The correlation information may indicates a correlation where the smaller the size of a black portion of a melanophore is, the longer the elapsed time after death is, and the analysis unit may detect the size of the black portion of the melanophore as the state of the melanophore of the fish. The size of the black portion of the melanophore may be expressed as area or the like calculated from the number of pixels corresponding to that black portion, for example. Accordingly, the amount of time elapsed since the death of the fish can be determined from the size of the black portion that can be identified by relatively simple calculation, such as calculation of area or the like.

The correlation information may indicate a correlation where the lower the degree of complexity of the shape of a black portion of a melanophore is, the longer the elapsed time after death is, and the analysis unit may detect the degree of complexity of the shape of the black portion of the melanophore as the state of the melanophore of the fish. The degree of complexity of the shape of the black portion of the melanophore can be expressed as a ratio of the length of the outline of the black portion as to the circumference of a circle having the same area as the black portion, for example. Accordingly, the amount of time elapsed since the death of the fish can be determined suitably according to the shape of the black portion in the melanophore due to movement of black pigment granules therein.

The state of the melanophore in the correlation information may be indicated in the form of features including the area of the black portion of the melanophore and the degree of complexity of the shape of the black portion, and the analysis unit may detect the features as the state of the melanophore of the fish. Accordingly, the amount of time elapsed since the death of the fish can be appropriately determined based on the features in the image.

The image of the fish acquired by the acquisition unit may be an image photographed by irradiating the fish with light including an ultraviolet region. Accordingly, the pigment granules of the melanophore absorb the ultraviolet rays and are differentiated from other portions. Thus, detection of the state of melanophores can be appropriately performed, and the amount of time elapsed since the death of the fish can be appropriately determined.

An elapsed-time determination method according to an aspect of the present disclosure includes: acquiring an image of a fish; analyzing the acquired image to detect a state of melanophores of the fish; and determining an amount of time elapsed since death of the fish in accordance with the state of the detected melanophores of the fish, based on correlation information indicating a correlation between the state of the melanophores of the fish and the amount of time elapsed since the death of the fish. Accordingly, determination of the amount of time elapsed since the death of the fish can be performed without marring the fish and without depending on the boundary position between the pupil and white of the eye.

A non-transitory computer-readable recording medium storing a control program according to an aspect of the present disclosure causes a computer in which the control program has been installed to execute elapsed-time determination processing, the elapsed-time determination processing including: acquiring an image of a target fish; analyzing the acquired image to detect a state of melanophores of the fish; and determining an amount of time elapsed since death of the fish in accordance with the state of the detected melanophores of the fish, based on correlation information indicating a correlation between the state of the melanophores of the fish and the amount of time elapsed since the death of the fish. The amount of time elapsed since the death of the fish can be determined by a computer in which this control program has been installed.

A preservation state determination apparatus according to an aspect of the present disclosure includes: a storage unit that stores correlation information indicating correlation between a state of melanophores of a fish and an amount of time elapsed since death of the fish in non-freezing cases; an acquisition unit that acquires an image of the fish; an analysis unit that analyzes the image acquired by the acquisition unit to detect the state of the melanophores of the fish; an elapsed-time determination unit that determines the amount of time elapsed since the death of the fish in non-freezing cases, in accordance with the state of the melanophores of the fish detected by the analysis unit, based on the correlation information; and a preservation state determination unit that determines a preservation state of the fish using the amount of time elapsed since the death of the fish determined by the elapsed-time determination unit, and outputs the determination results. Accordingly, the preservation state of the fish can be determined by image analysis.

The preservation state determination apparatus may further include an input unit that accepts input of the amount of time elapsed since the death of the fish in the image acquired by the acquisition unit, with the preservation state determination unit determining whether the state of the fish is a frozen state or not, by comparing the elapsed time from the input accepted by the input unit and the elapsed time determined by the elapsed-time determination unit. The concept of the input that the input unit accepts is not restricted to input of information by human operations, and includes receiving information from internal/external devices of the preservation state determination unit, and acquiring information by reading out information from a recording medium. Accordingly, the preservation state of whether the fish has been preserved by freezing or not, which is difficult to distinguish from appearance, can be suitably determined from the amount of time elapsed since death that has been input and images suitable for analysis of melanophores.

The preservation state determination apparatus may further include an input unit that accepts input of the amount of time elapsed since the death of the fish in the image acquired by the acquisition unit. The storage unit may store correlation information indicating the correlation between the state of melanophores of the fish and the amount of time elapsed since the death of the fish at each of multiple temperatures in a non-freezing temperature range. The elapsed-time determination unit may determine the amount of time elapsed since the death of the fish at each of the multiple temperatures, in accordance with the state of the melanophores of the fish detected by the analysis unit, based on the correlation information for that temperature. The preservation state determination unit may determine the temperature at which the fish was preserved as the preservation state of the fish, by comparing the elapsed time from the input accepted by the input unit and each elapsed time determined by the elapsed-time determination unit. Accordingly, the temperature at which the fish has been preserved can be estimated based on input of the amount of time elapsed since the death of the fish, and image analysis.

The image of the fish acquired by the acquisition unit may be an image photographed including part of an iris or fin of the fish. Accordingly, an image can be analyzed which is suitable for analyzing melanophores so determination of the preservation state of the fish can be performed in a suitable manner.

The correlation information may indicate correlation between features including the area of black portions of the melanophores and the degree of complexity of shape of the black portions, and elapsed time since death, with the analysis unit detecting the features as the state of the melanophores of the fish. Accordingly, the preservation state of the fish can be estimated more suitably by features in the image.

The correlation information may indicate correlation where the smaller the size of the black portions of the melanophores is, the longer the elapsed time since death is, or correlation where the smaller the degree of complexity of the shape of the black portions of the melanophores is, the longer the elapsed time since death is. When the correlation information indicates that the smaller the size of the black portions of the melanophores is, the longer the elapsed time since death is, the analysis unit may detect the size of the black portions of the melanophores as the state of the melanophores of the fish. When the correlation information indicates that the smaller the degree of complexity of the shape of the black portions of the melanophores is, the longer the elapsed time since death is, the analysis unit may detect the degree of complexity of the shape of the black portions of the melanophores as the state of the melanophores of the fish. Accordingly, the size or shape of the black portions of the melanophores of the fish can be used to suitably determine the preservation state of the fish.

The preservation state determination unit may determine whether or not the fish has been preserved by freezing, based on this comparison. In a case where the determined elapsed time is shorter than the input elapsed time, the preservation state determination unit may determine that the fish has been preserved by freezing. Accordingly, the user can know whether or not the fish has been preserved by freezing.

The image of the fish acquired by the acquisition unit may be an image acquired by photographing light reflecting at a predetermined depth from the surface of the fish. Accordingly, the preservation state of the fish can be suitably determined by deciding a depth where many melanophores are present, as the predetermined depth.

The image of the fish acquired by the acquisition unit may be an image with resolution higher than resolution of 2 µm per pixel. The correlation information may indicate correlation where the smaller the degree of complexity of the shape of the black portions of the melanophores is, the longer the elapsed time since death is. The analysis unit may detect the degree of complexity of the shape of the black portions of the melanophores as the state of the melanophores of the fish. Accordingly, the shape of the black portions of the melanophores of the fish can be analyzed in a precise manner, and the preservation state of the fish can be suitably determined.

The acquisition unit may acquire the image from a camera that photographs images of the fish, and the preservation state determination apparatus may further include a judgment unit that judges whether or not the ratio of a black region extracted from the image as to the entire image is within a certain range, and an output unit that outputs a message prompting moving of the camera in a case where the judgment unit has judged that the ratio is not within the certain range. Accordingly, an image suitably for analysis of the melanophore of the fish can be obtained as a result of having prompted the user to move the camera, so the preservation state of the fish can be determined in a suitable manner.

The preservation state determination unit may determine an amount of time taken from landing the fish to completion of freezing, in accordance with the determined elapsed time, and may determine that the longer the determined elapsed time is, the longer the time taken from landing the fish to completion of freezing has been. Thus, the user can know the amount of time taken from landing the fish to completion of freezing.

The acquisition unit may acquire an image generated by photographing at the same time multiple fish frozen at the same time by a freezing apparatus. The preservation state determination unit may determine what sort of freezing apparatus having what sort of freezing capabilities the multiple fish have been preserved by, based on distribution of elapsed time after death determined by the elapsed-time determination unit regarding the multiple fish. Accordingly, the user can know of the freezing capabilities of the freezing apparatus that has frozen the fish.

A preservation state determination method according to an aspect of the present disclosure includes: acquiring an image of a fish; analyzing the image acquired in the acquiring to detect a state of melanophores of the fish; determining an amount of time elapsed since death of the fish in non-freezing cases, in accordance with the state of the melanophores of the fish detected in the analyzing, based on correlation information indicating correlation between the state of the melanophores of the fish and the amount of time elapsed since the death of the fish in a non-freezing case; and determining a preservation state of the fish using the amount of time elapsed since the death of the fish that has been determined. Accordingly, the preservation state of the fish can be determined.

A non-transitory computer-readable recording medium storing a control program according to an aspect of the present disclosure causes a computer in which the control program has been installed to execute preservation state determination processing, the preservation state determination processing including: acquiring an image of a fish; analyzing the image acquired in the acquiring to detect a state of melanophores of the fish; determining an amount of time elapsed since death of the fish in non-freezing cases, in accordance with the state of the melanophores of the fish detected in the analyzing, based on correlation information indicating correlation between the state of the melanophores of the fish and the amount of time elapsed since the death of the fish in a non-freezing case; and determining a preservation state of the fish using the amount of time elapsed since the death of the fish that has been determined. Accordingly, the preservation state of the fish can be determined by a computer in which this control program has been installed.

An elapsed-time information output apparatus according to an aspect of the present disclosure includes: an acquisition unit that acquires an image of a fish; an analysis unit that analyzes the image acquired by the acquisition unit to detect a state of melanophores of the fish; and an output unit that outputs information indicating an amount of time elapsed since death of the fish, determined in accordance with the state of melanophores of the fish detected by the analysis unit, determined based on correlation information indicating correlation between the state of the melanophores of the fish and the amount of time elapsed since the death of the fish. Thus, the amount of time elapsed since the death of the fish can be recognized.

A preservation state information output apparatus according to an aspect of the present disclosure includes: an acquisition unit that acquires an image of a fish; an analysis unit that analyzes the image acquired by the acquisition unit to detect a state of melanophores of the fish; an input unit that accepts input of an amount of time elapsed since death of the fish in the image acquired by the acquisition unit; and an output unit that outputs information indicating regarding whether or not a state of the fish is a frozen state, based on the relationship between the amount of time elapsed since the death of the fish in a non-freezing case, determined in accordance with the state of melanophores of the fish detected by the analysis unit, determined based on correlation information indicating correlation between the state of the melanophores of the fish and the amount of time elapsed since the death of the fish in a non-freezing state, and the elapsed time in the input accepted by the input unit. Thus, a preservation state of the fish can be recognized.

A preservation state information output apparatus according to an aspect of the present disclosure includes: memory that stores correlation information indicating correlation between a state of melanophores of a fish and an amount of time elapsed since death of the fish in a non-freezing case; a processor that identifies the amount of time elapsed since the death of the fish in a non-freezing case, based on the correlation information, in accordance with the state of the melanophores in an image of the fish that has been input, identifies a preservation state of the fish in accordance with the identified elapsed time, and outputs preservation state information indicating the identified preservation state; and a display that displays the preservation state information output from the processor. Accordingly, the user can confirm the preservation state of the fish in the display, without marring the fish.

A deciding apparatus according to an aspect of the present disclosure includes: an acquisition unit that acquires a first image that includes an image of a target fish; an analysis unit that acquires first information of a melanophore of the target fish from the first image; a storage unit that stores correlation information indicating correlation between information of a melanophore of a fish and an amount of time elapsed since death of the fish; an elapsed-time deciding unit that decides an amount of time elapsed since death of the target fish, based on the first information and the correlation information; and a preservation state deciding unit that decides a preservation state of the target fish based on the decided elapsed time and information of the target fish.

The deciding apparatus may further include: an input unit that accepts input information, which is information of the target fish, wherein the information of the target fish is the amount of time elapsed since the death of the target fish, wherein the preservation state of the fish is room temperature, wherein a preservation state of the target fish is whether a frozen preservation state or not, and wherein deciding of the preservation state of the target fish is further performed based on the input information.

The deciding apparatus may further include: an input unit that accepts input information, which is information of the target fish, wherein the information of the target fish is the amount of time elapsed since the death of the target fish, wherein deciding of the preservation state of the target fish is further performed based on the input information, wherein the correlation information includes first correlation information, second correlation information, and third correlation information. The first correlation information may indicate correlation between information of a melanophore of the fish and an amount of time elapsed since death of the fish under a condition that the fish is preserved at ice temperature, the second correlation information may indicate correlation between information of a melanophore of the fish and an amount of time elapsed since death of the fish under a condition that the fish is preserved at refrigeration temperature, the third correlation information may indicate correlation between information of a melanophore of the fish and an amount of time elapsed since death of the fish under a condition that the fish is preserved at room temperature, and the preservation state may include any one state of a frozen preservation state, an ice temperature preservation state, a refrigeration temperature preservation state, and a room temperature preservation state.

The first image may include an image of all or part of a fin of the target fish, or an image of an iris of the target fish.

The correlation information may indicate a correlation where the shorter the perimeter of a black portion of a melanophore is, the longer the elapsed time after death of the fish is.

The correlation information may indicate a correlation where the smaller the average value of areas of black portions of melanophores is, the longer the elapsed time after death of the fish is.

In a case where the amount of time elapsed since the death of the target fish decided based on the first correlation information is shorter than the amount of time elapsed since the death of the target fish that the input information indicates, the preservation state deciding unit may decide that the preservation state of the target fish is the frozen preservation state.

The first image may be generated by imaging reflected light acquired by irradiating the target fish with light that has passed through a first polarization filter, the reflected light being light that has passed through a second polarization filter orthogonal to the first polarization filter.

The first image may be an image with resolution higher than resolution of 2 μm per pixel.

The target fish may be a first target fish, the first image may include an image of a second target fish, the first target fish and the second target fish may have been frozen at the same time by a freezing apparatus, the analysis unit may acquire second information of a melanophore of the second target fish from the first image, the elapsed-time deciding unit may decide an amount of time elapsed since death of the second target fish, based on the correlation information, and freezing capabilities of the freezing apparatus may be decided based on the amount of time elapsed since the death of the first target fish and the amount of time elapsed since the death of the second target fish that have been decided.

A deciding apparatus according to an aspect of the present disclosure includes: an acquisition unit that acquires a first image of a target fish; an analysis unit that acquires first information of a melanophore of the target fish from the first image; a storage unit that stores correlation information indicating correlation between information of a melanophore of a fish and an amount of time elapsed from landing of the fish to freezing; and a determination unit that determines an amount of time elapsed from landing of the target fish to freezing, based on the first information and the correlation information.

A deciding method according to an aspect of the present disclosure includes; acquiring a first image of a target fish; acquiring first information of a melanophore of the target fish from the first image; storing correlation information indicating correlation between information of a melanophore of a fish and an amount of time elapsed since death of the fish; deciding an amount of time elapsed since death of the target fish, based on the first information and the correlation information; and deciding a preservation state of the target fish based on the decided amount of time elapsed and information of the target fish.

A non-transitory computer-readable recording medium storing a control program according to an aspect of the present disclosure causes an apparatus including a processor to executing a deciding method including acquiring a first image of a target fish, acquiring first information of a melanophore of the target fish from the first image, storing correlation information indicating correlation between information of a melanophore of a fish and an amount of time elapsed since death of the fish, deciding an amount of time elapsed since death of the target fish, based on the first information and the correlation information, and deciding a preservation state of the target fish based on the decided elapsed time and information of the target fish.

In the present disclosure, the elapsed-time determination apparatus, elapsed-time information output apparatus, preservation state determination apparatus, and preservation state information output apparatus, may be referred to as a "deciding apparatus". Also, in the present disclosure, the elapsed-time determination method, elapsed-time information output method, preservation state determination method, and preservation state information output method, may be referred to as a "deciding method".

These comprehensive or specific embodiments may be implemented as a system, a method, an integrated circuit, a computer program, or a computer-readable recording medium such as a CD-ROM, or any combination of a system, method, integrated circuit, computer program, and recording medium.

The elapsed-time determination apparatus, preservation state determination apparatus, and so forth, according to embodiments of the disclosure, will now be described with reference to the drawings. Note that each of the embodiments described below indicate a preferred specific example of the present disclosure. That is to say, values, shapes, materials, components, placement and connection arrangement of components, steps (procedures), orders of steps, and so forth in the following embodiments are only exemplary, and are not intended to restrict the present disclosure. Accordingly, components in the following embodiments which are not included in an independent Claim of the present disclosure indicating the highest concept are described as being components which are not necessarily indispensable in achieving solving of the problem but make up a more preferable form. It should also be noted that the drawings are schematic diagrams, and are not exact illustrations.

Overview

Determining an amount of time elapsed after death of a fish by analyzing a photographed image of the fish, without marring the fish, is effective as a method to judge the freshness of fish on the market. The elapsed-time determination apparatus according to the embodiments is an apparatus that detects a state of melanophores in the irises or fins of fish by analyzing a photographed image of the fish, and determines the amount of time elapsed from death of the first or the preservation state of the fish, from the state of the melanophores. These melanophores are widely found in the epidermis, for example, of fish. The determination according to these apparatuses is based on a discovery made by the present Inventors, that there is a particular correlation between the state of melanophores in the irises and fins (dorsal fin, caudal fin, etc.) of fish, and the amount of time elapsed since the death of the fish. The present inventors observed change in melanophores of freshwater fish (Japanese dace and common carp) over time from death.

FIG. 1 is a set of image obtained by photographing a part of the iris 71 of the eye 70 of a Japanese dace, magnified 200 times. Images 71a through 71f are images taken of the fish at room temperature, once every hour from four hours after death to nine hours. These images are converted from color images in which they were show by a visible-light camera into grayscale, and binarized. Note that melanophores can be photographed by visible-light cameras, infrared cameras, and ultraviolet light cameras, for example. A portion surrounded by a circle in the images 72a through 72f includes a single melanophore. The pigment granules of the melanophore encircled by circles 72a in image 71a can be seen spreading in a complex shape with many protrusions, which is the shape of the melanophore cell, and the area over which the pigment granules are spread is wide. The black portion of the melanophore, which is the area over which the pigment granules are spread, gradually loses the protrusions over time, and by nine hours after death, the area of the pigment granules in the circle 72f in image 71f is small and is close to a simple circle.

Figure 2B:
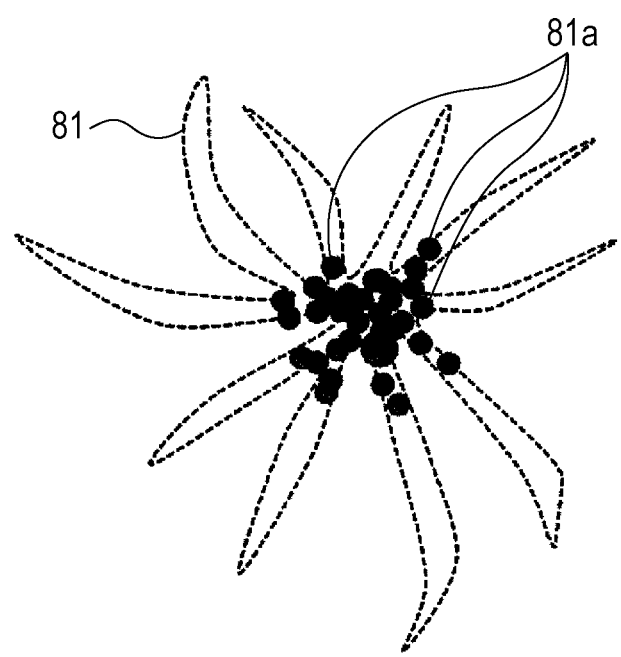
FIG. 2B is a schematic diagram illustrating a distribution state (aggregated state) of pigment granules in a melanophore.

FIGS. 2A and 2B are a schematic diagrams illustrating distribution states of pigment granules (melanin granules) in a melanophore. FIG. 2A illustrates the distribution (dispersed) of pigment granules 80a throughout a melanophore 80, and FIG. 2B illustrates a state where pigment granules 81a are aggregated at the middle of a melanophore 81. For example, the pigment granules of the melanophore encircled by the circle 72a in image 71a are spread throughout the entire melanophore as illustrated in FIG. 2A, so the area of the pigment granules of the melanophore has a shape that is complex and has many protrusions, and the area covered is wide as well. After passage of time from the death of the fish, the pigment granules of the melanophore encircled by the circle 72f in image 71f are spread aggregated at the middle portion of the melanophore as illustrated in FIG. 2B, and the pigment granules of the melanophore form a small circle.

The present Inventors have thus discovered that the pigment granules of the melanophores in the irises and fins of fish that have not been chemically treated after death aggregate over time. On the other hand, it has been confirmed that there is no change in the area of pigment granules in melanophores over time in the scales on the sides of the fish.

Accordingly, the amount of time elapsed since the death of a fish, for example, can be suitably determined using the correlation between the state of melanophores in the iris or fins of the fish and the amount of time elapsed after the death of the fish, by analyzing images of the fish using the elapsed-time determination apparatus according to the embodiments. Japanese Unexamined Patent Application Publication No. 2002-360223 notes that salmon, trout, and sparidae exhibit increase in the black area of melanophores due to spreading of melanin which is the pigment granules in the melanophores after death of the fish, particularly at the belly of the fish. This is a different phenomenon from the aggregation of pigment granules of the melanophores over time in the iris and fins which the present Inventors have discovered.

First Embodiment

Description will be made in the first embodiment of an elapsed-time determination apparatus that determines an amount of time elapsed since death of a fish, by acquiring an image of an iris or fin of the fish and analyzing the image based on the above-described discovery. An elapsed-time determination apparatus 10 according to the present embodiment is configured including an Input unit, a storage device which is memory for example, an image acquisition unit which is an imaging sensor of a camera for example, and output device which is a display for example, and a computer having a processor for example. Note that the image acquisition unit may be a scanner which reads photographs and generates images, for example, a device which reads image data from a recording medium in which is recorded an image taken by the image sensor of the camera, or the like. The memory stores a control program for causing the processor to execute elapsed-time determination processing, for example, and is used to share data used by the processor at the time of the elapsed-time determination processing.

The elapsed-time determination apparatus 10 has the function of executing the elapsed-time determination processing according to the elapsed-time determination method. That is to say, the elapsed-time determination apparatus 10 has the function of performing image processing of acquired images of fish, and calculating the area of portions corresponding to black pigment particles in melanophores. The elapsed-time determination apparatus 10 also has the function of determining an amount of time elapsed since death, based on correlation information, which is information stored beforehand that gives the correlation between the black portions in melanophores and the amount of time elapsed since death, in accordance with the calculated area.

Figure 3:
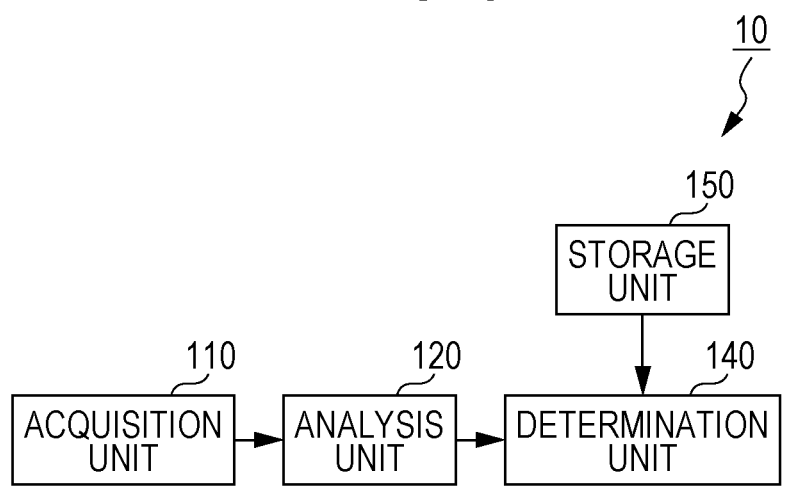
FIG. 3 is a functional block diagram illustrating the configuration of an elapsed-time determination apparatus according to a first embodiment.

FIG. 3 is a functional block diagram illustrating the configuration of the elapsed-time determination apparatus 10 according to the first embodiment. The elapsed-time determination apparatus 10 includes an acquisition unit 110, an analysis unit 120, a determination unit 140, and a storage unit 150, as illustrated in FIG. 3.

The acquisition unit 110 is realized by a processor that executes the control program, and an image acquisition device, and has the function of acquiring an image (still image) where the fish has been shot. This image is taken by a camera, for example, capable of photographing at wavelengths of any one range of ultraviolet light, visible light, and infrared light. Note that melanin granules included in the melanophore, which are the pigment granules, are of a substance that absorbs ultraviolet rays. Accordingly, an image obtained by photographing using ultraviolet rays is effective in clearly distinguishing between portions that contain pigment granules and portions that do not contain pigment granules.

The function of the analysis unit 120 is realized by the processor that executes the control program. The analysis unit 120 has the function of detecting the state of the melanophores of the fish, by analyzing the image acquired by the acquisition unit 110. The analysis unit 120 includes an image processing unit 120a and a melanophore state analysis unit 120b. The image processing unit 120a has a function of performing image processing to extract the black portions of the melanophores in the image acquired by the acquisition unit 110. The melanophore state analysis unit 120b has a function of analyzing the state of black portions of the melanophores in the image subjected to processing at the image processing unit 120a. The image processing unit 120a and melanophore state analysis unit 120b will be described in detail later.

The storage unit 150 is realized by a region of a storage device, and stores correlation information representing the correlation between the state of black portions of melanophores of fish and the amount of time elapsed since the death of the fish, generated beforehand based on experimentation where change in the state of melanophores over time was measured. The correlation information may be a table that stores elapsed time and the state of melanophores, or may store a function of the state of melanophores as to the elapsed time. In the present embodiment, the state of melanophores is expressed by the size (area) of the black portion of a melanophore. In this case, the correlation information represents the correlation where the smaller the area of the black portion of a melanophore is, the longer the amount of time elapsed since death. Note that the storage unit 150 may be configured using cache memory or the like, or may receive correlation information from an external device (e.g., a server device communicable with the elapsed-time determination apparatus 10 over a network), for example, and temporarily store the correlation information. The storage unit 150 may also read out and acquire correlation information from a recording medium, and store this correlation information.

The determination unit 140 has functions of referencing the correlation information stored in the storage unit 150, judging what state according to time elapsed since death the state of the melanophore analyzed by the melanophore state analysis unit 120b corresponds to, determining the amount of time elapsed since the death of the fish, and outputting the determination results. This determination unit 140 is realized by the processor that executes the control program, and the output device.

Figure 4:
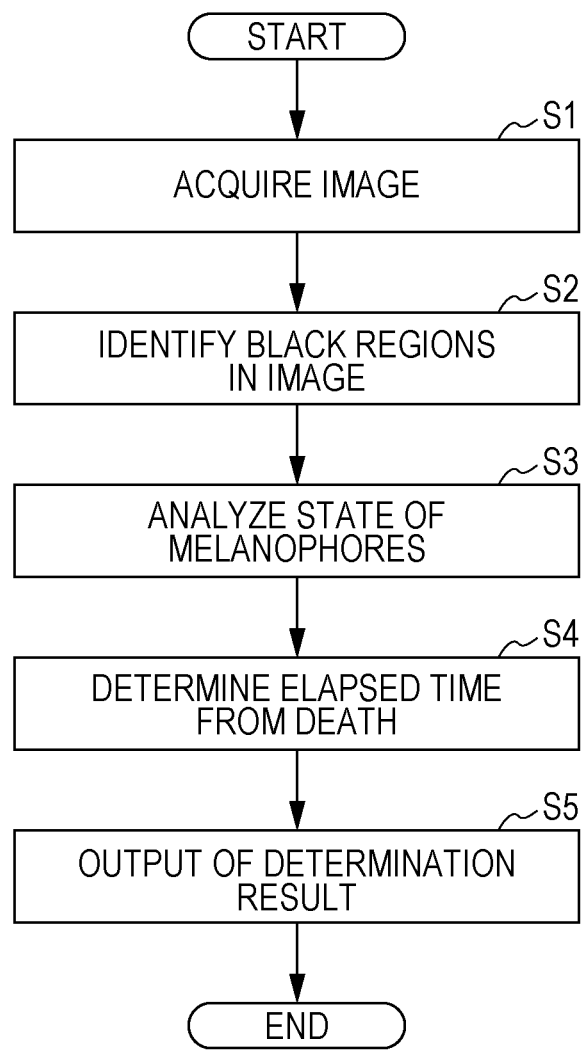
FIG. 4 is a flowchart illustrating elapsed-time determination processing according to the first embodiment.

FIG. 4 is a flowchart illustrating the elapsed-time determination processing by the elapsed-time determination apparatus 10 according to the present embodiment. The processing procedures in the elapsed-time determination processing will be described following FIG. 4. This elapsed-time determination processing is started by input to the input unit of the elapsed-time determination apparatus 10 (e.g., by pressing a switch).

First, the acquisition unit 110 of the elapsed-time determination apparatus 10 acquires a still image from the acquisition device (step S1). This image includes an iris or fin of the fish.

The image processing unit 120a of the analysis unit 120 identifies black regions in the image by performing image processing on the acquired image (step S2). This image processing will be described later in detail.

Next, the melanophore state analysis unit 120b of the analysis unit 120 extracts melanophores from the black regions identified in step S2, and detects the state of the melanophores by analyzing the melanophores (step S3). The size of the black portions of the melanophores, serving as the state of the melanophores, is detected by extracting continuous black regions, and calculating the area for each region. The area is calculated from the number of pixels included in a region extracted as a black region, using information of actual distance between pixels which is the pixel pitch of the image or the actual area per pixel. The information of the actual distance between pixels or the actual area per pixel is acquired as additional information at the same time as the acquisition unit 110 acquiring the image, or the elapsed-time determination apparatus 10 storing predetermined information in memory, for example, beforehand.

Next, the determination unit 140 determines the amount of time elapsed since the death of the fish by referencing the correlation information stored in the storage unit 150 (step S4), based on the state of the black region detected in step S3 by the analysis unit 120 (melanophore state analysis unit 120b), and outputs the determination results (step S5). Note that the state of the black region here specifically is the area of the black portion. The determination will be described in detail later. The output in step S5 is display of text or images, for example, if the output device is a display. The output may be audio output or printed output instead. In a case of audio output, an audio output device (e.g., a speaker) may be used as the output device. In a case of printing output, a printer may be used as the output device.

Thus, the elapsed-time determination apparatus 10 analyzes the state of melanophores from an image of a fish acquired from the elapsed-time determination apparatus 10, and determines the amount of time elapsed since the death of the fish.

Next, detailed configurations and operations of the image processing unit 120a and melanophore state analysis unit 120b of the analysis unit 120 will be described. Hg. 5 is a block diagram illustrating an exemplary detailed configuration of the analysis unit 120 according to the first embodiment.

Figure 5:
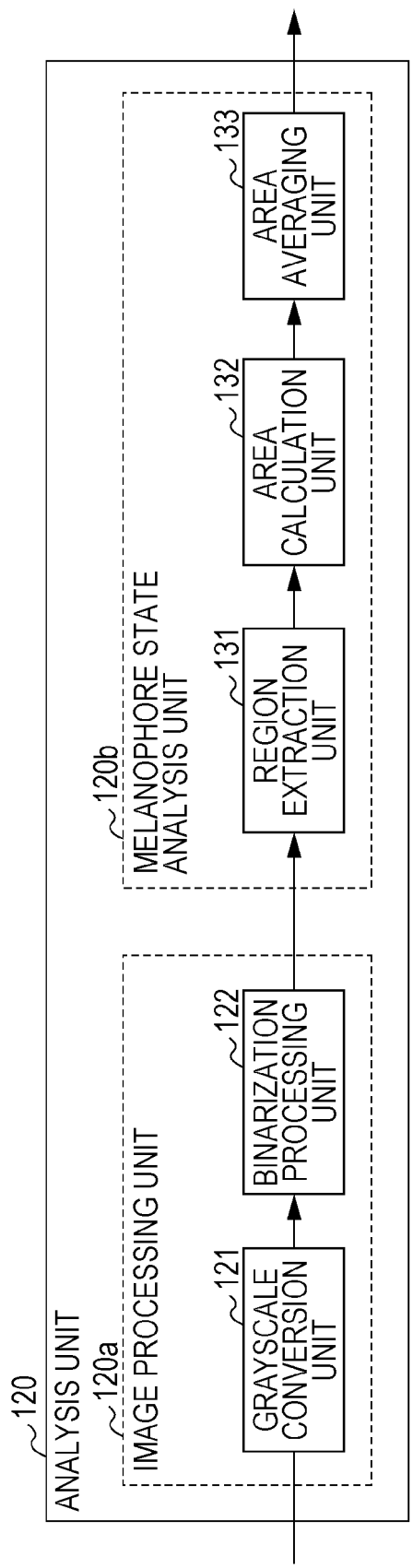
FIG. 5 is a block diagram illustrating an exemplary detailed configuration of an analysis unit according to the first embodiment.

First, the image processing unit 120a will be described in detail. The image processing unit 120a includes a grayscale conversion unit 121 and a binarization processing unit 122, as illustrated in FIG. 5.

The grayscale conversion unit 121 receives the image the acquisition unit 110 has acquired, and converts the color image into a grayscale image (monochrome image). Conversion to a grayscale image is performed by the weighted average method using National Television System Committee (NTSC) coefficients, for example. A calculation method using NTSC coefficients is described below.

In a case where the three values of red R, green G, and blue B are any integer of 0 to 255, a post-grayscale-conversion value Y which is an integer in the range of 0 to 255 is obtained by the following expression.

$$Y=(0.298912 \times R+0.586611 \times G+0.114478 \times B)$$

Other methods besides calculation by NTSC coefficients may be used for conversion to grayscale, such as calculation by HDTV coefficients, the simple average method, or the like.

The binarization processing unit 122 performs processing of setting a threshold value for the luminance of each pixel in the image converted into a grayscale image by the grayscale conversion unit 121, and assigning white to pixels with a luminance exceeding the threshold value, and black to pixels with a luminance equal to or below the threshold value. A predetermined value may be applied as the threshold value, or a luminance distribution may be obtained for each image and the threshold value decided based on this distribution. The method for deciding the threshold value is deciding such that both white and black exist to a certain extent, such as two thirds of the pixels being white and a third of the pixels being black, for example.

Figure 6:
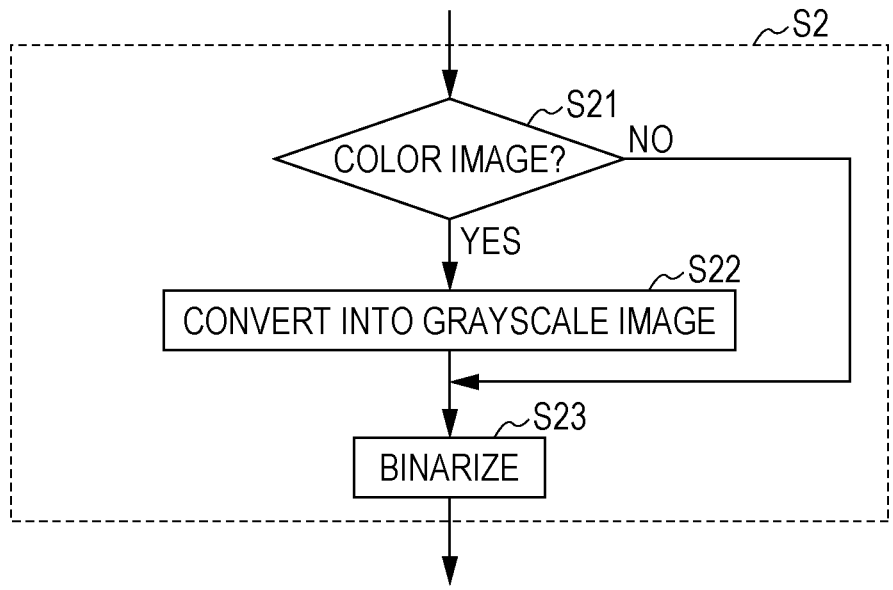
FIG. 6 is a flowchart illustrating a partial detailed example of elapsed-time determination processing according to the first embodiment.

FIG. 6 is a flowchart illustrating a partial detailed example of elapsed-time determination processing according to the first embodiment. Detailed operations of the identifying of the black region in step S2 in FIG. 4 will be described following FIG. 6.

The grayscale conversion unit 121 judges whether the image which the acquisition unit 110 has acquired is a color image or a monochrome image (step S21). This judging is made at the time of the acquisition unit 110 acquiring the image, by acquiring information appended to the image regarding whether a color image or a monochrome image and judging based on this information. In a case where no monochrome images are input and just color images are input, this judgment may be omitted.

In a case of having judged that the image which the acquisition unit 110 has acquired is a color image, the grayscale conversion unit 121 converts the color image acquired by the acquisition unit 110 into a grayscale image (step S22).

In a case where judgment has been made in step S21 that the image which the acquisition unit 110 has acquired is not a color image, and in a case where step S22 has been executed, the binarization processing unit 122 binarizes the grayscale image (step S23). The black portions of this binarized image make up the black regions. While description has been made here regarding a method of binarizing the acquired image based on luminance to identify the black portions making up the black regions, the black portions may be identified using other color differentiation methods or the like.

Next, the melanophore state analysis unit 120b will be described in detail. The melanophore state analysis unit 120b includes a region extraction unit 131, area calculation unit 132, and an area averaging unit 133, as illustrated in FIG. 5. The region extraction unit 131 separates the image binarized at the image processing unit 120a where the back portions have been identified into individual clumps which are clusters of continuous black-portion pixels, and extracts each dump as a black region.

The area calculation unit 132 calculates the area of each of one or more black regions extracted by the region extraction unit 131. The area of a region is calculated as the product of the total number of pixels in the black region made up of continuous black pixels extracted by the region extraction unit 131, and the actual area per pixel. Information of the actual area per pixel is acquired as appended information at the same time as the acquisition unit 110 acquiring the image, or the elapsed-time determination apparatus 10 storing a predetermined actual area per pixel in memory, for example. Note that the actual area per pixel is decided by the distance between the camera and the subject, or the magnification of the lens, for example. The area averaging unit 133 averages the calculated areas of black regions.

Figure 7:
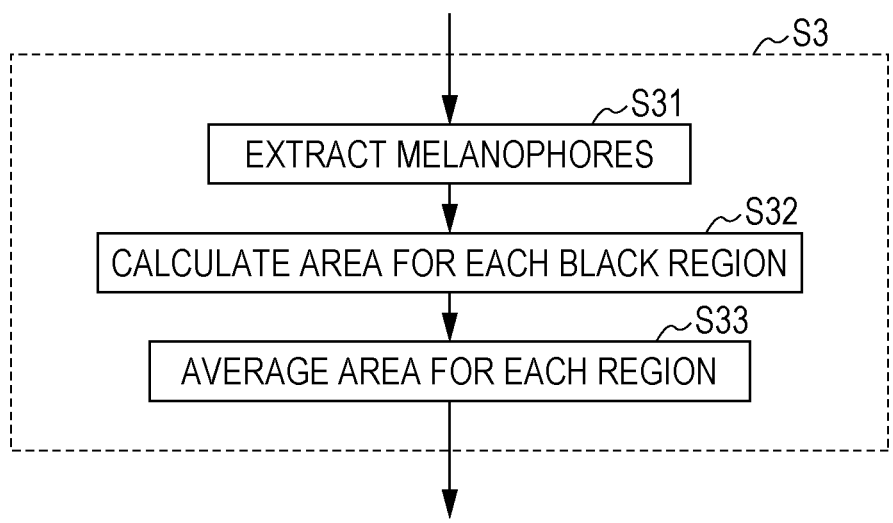
FIG. 7 is a flowchart illustrating a partial detailed example of elapsed-time determination processing according to the first embodiment.

FIG. 7 is a flowchart illustrating a partial detailed example of elapsed-time determination processing according to the first embodiment. Detailed operations of the analysis of melanophores (detection of the state of melanophores) in step S3 illustrated in FIG. 4 will be described following FIG. 7.

The region extraction unit 131 extracts each black region, which is consecutive black portions in the image binarized in step S23, as a melanophore (step S31). For example, in image 71a in FIG. 1 the black region encircled by the circle 72a is extracted as a single melanophore, and in image 71e in FIG. 1 three black regions are extracted as three melanophores.

The area calculation unit 132 calculates the area for each of the one or more melanophores extracted in step S31 (step S32). The area is the product of the actual area per pixel and the total number of pixels in the region, for example. In a case where each pixel is 4 µm² for example, meaning that the actual distance between pixels which is the pixel pitch is 2 µm, and the number of pixels in a black region extracted as a melanophore is 6,000, the area is 24,000 µm². The area averaging unit 133 averages the areas of the one or more melanophores calculated in step S32 (step S33). Detection of the state of the melanophores (size of the black portions) is realized by this calculation of average area.

There may be cases where black portions of multiple melanophores are connected as illustrated at the lower right in image 71a in FIG. 1, and this may be judged to be a single continuous black region which is extracted as a single melanophore in step S31. In a case where the area of such a black region is unrealistically large for a melanophore, that black region may be excluded from extraction as a melanophore in step S31, and thus excluded from averaging in step S33. That is to say, black regions larger than a predetermined size (e.g., diameter of 500 µm) may be excluded.

Although description has been made regarding calculation of the average value of areas of melanophores in order to detect the size of black portions serving as the state of the melanophores, the size of the black portions of melanophores may be detected by other methods, such as expressing the size of the black portions of melanophores in terms of the radius or diameter or the like of a circle of the same area, for example. Alternatively, statistical representative values such as median value of the areas of the melanophores, variance of the areas of the melanophores, and so forth, may be used, for example.

Figures 8, 9:
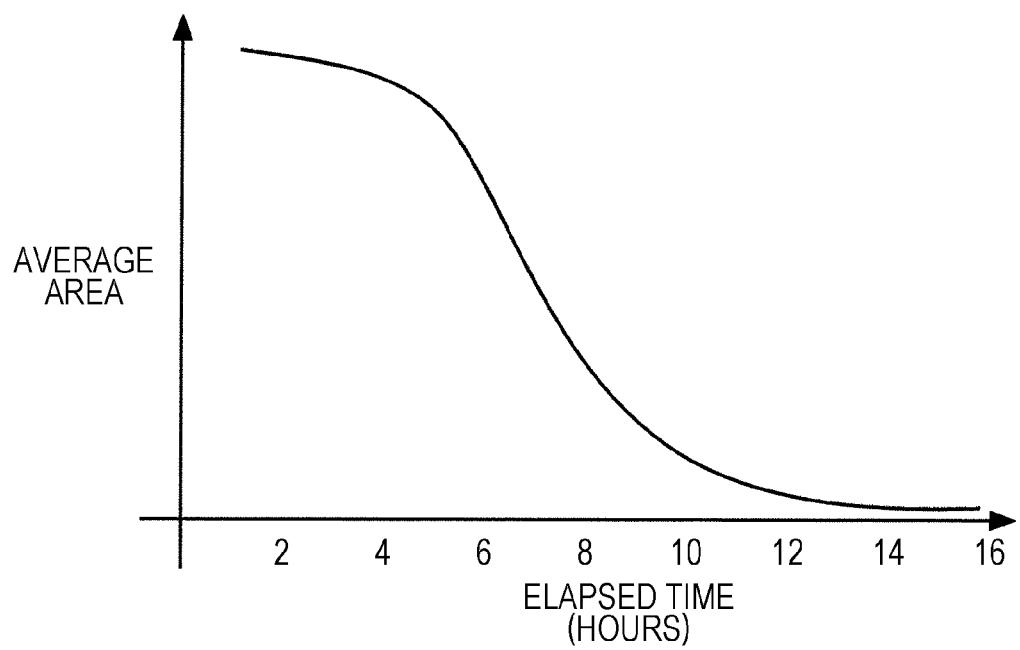
FIG. 8 is a diagram illustrating an example of correlation information stored in a storage unit according to the first embodiment.
FIG. 9 is an exemplary function graph illustrating change in average area over time.

The following is a specific example of processing of determining the amount of time elapsed since the death of the fish (step S4) based on correlation information according to the detection results of the state of the melanophores described above. FIG. 8 is a diagram illustrating an example of correlation information stored in the storage unit 150. In this example, the correlation information is stored in the storage unit 150 as a table where the state of melanophores, i.e., the average area, and elapsed time have been correlated. In this example, the correlation between this average area and elapsed time has been found through experimentation, for example, and elapsed time represents the amount of time elapsed since the death of the fish when preserved at room temperature. The experimentation may have obtained the average area of melanophores on a fish and the amount of time elapsed since the death of the fish when preserved at room temperature from multiple specimens of fish.

The determination unit 140 determines and outputs the amount of time elapsed since the death of the fish based on the correlation information, in accordance with the size (area) of black portions serving as the state of the melanophores of the fish, detected in step S3. For example, in a case where the average area of melanophores detected is 24,000 $\mu m^2$, this falls in the range of 10,000 $\mu m^2$ or larger but smaller than 50,000 $\mu m^2$ according to the correlation information exemplified in FIG. 8 so the amount of time elapsed since the death of the fish is determined to be between 6 to 8 hours.

Note that the storage unit 150 may store correlation information representing the correlation between the average area of melanophores and the amount of time elapsed since the death of the fish in another format instead of storing as the above-described table. For example, the storage unit 150 may store parameters defining functions representing the change in average area over time. In this case, the determination unit 140 determines elapsed time by calculating the elapsed time from average area using a function determined by parameters stored in the storage unit 150. FIG. 9 is an exemplary function graph illustrating change in average area over time. The correlation information may be stored and referenced in a format other than a table or a function.

Although description has been made above that the elapsed time is at room temperature, the correlation information may represent the correlation between size of black portions of melanophores and elapsed time at each of multiple preservation temperatures, in accordance with the temperatures at which fish to be handled by the elapsed-time determination apparatus 10 are preserved. This may include correlation at refrigeration temperature and ice temperature.

Description has been made in the present embodiment that one black region which is continuous black portions in the binary image is extracted as a single melanophore. Alternatively, an arrangement may be made where two types of threshold values for binarization are set a predetermined intervals, and black portions where the shape of consecutive black portions change according to difference in threshold values are extracted as melanophores. Images of melanophores are taken with the distribution of pigment granules in a cell being expressed as luminance distribution. Accordingly, except for cases where black pigment granules are uniformly dispersed throughout the melanophore or cases where all pigment granules are aggregated at the center portion, the outline of the melanophore becomes ambiguous, expressed in the form of a gradation where the luminance at the center portion of the melanophore is low and the luminance at the perimeter is high. Accordingly, the shape of many melanophores will change by changing the luminance threshold values for binarization. Thus, a black region of which the shape changes depending on difference in threshold values can be extracted as a melanophore, enabling differentiation from black portions with low luminance other than the iris melanophores, for example, and accordingly the precision of determination of time elapsed since death can be improved.

The image which the acquisition unit 110 acquires may be an image where the depth range from the surface of the fish is restricted. An example of a method to restrict the depth range is photography where light reflected from the surface of the fish is eliminated using a polarization filter. When the fish is illuminated using a polarization filter at the light source, light reflected at the surface maintains the polarization state, but light which enters the subject (fish) from the surface and reflects at inner substances becomes unpolarized light since the polarized state of the reflected light cannot be maintained. Placing a polarization filter orthogonal to the polarization filter used at the light source results in the reflected light maintaining the polarized state, that has been reflected at the surface, not being passed, and part of the unpolarized light reflected from within the subject passing the filter. Accordingly, the depth range from the surface of the fish can be set when acquiring an image. The melanophores are distributed closer to the surface of the dermis, so restricting the focal range to a depth where there are many melanophores allows black substances other than melanophores to be eliminated from the image. Also, it is known that light reaches difference depths from the surface depending on the frequency of the light. Adjusting the frequency of the light source to reflect at a predetermined depth where melanophores are present can yield the same advents as those of polarization.

First Modification of First Embodiment

An elapsed-time determination apparatus 20 according to a first modification of the first embodiment will be described. This elapsed-time determination apparatus 20 has the same hardware configuration as the elapsed-time determination apparatus 10 according to the first embodiment, but the control program executed by the processor is different, and accordingly functions differ somewhat, as follows.

The elapsed-time determination apparatus 10 detects the size of black portions (e.g., the area of the black portions) as the state of the melanophores, to serve as the basis for elapsed-time determination. In comparison with this, the elapsed-time determination apparatus 20 according to the first modification of the first embodiment detects the degree of complexity of the shapes of black portions, as the state of the melanophores, as an index used as the basis for elapsed-time determination. In a state where the pigment granules of a melanophore are dispersed, the black portion of the melanophore has a complex shape like a star, while black portions where the pigment granules have aggregated have a simple shape like a circle. Using the degree of complexity of the shape of the black portions as an index enables highly-precise elapsed-time determination to be performed reflecting the states of melanophores in detail.

Figure 10:
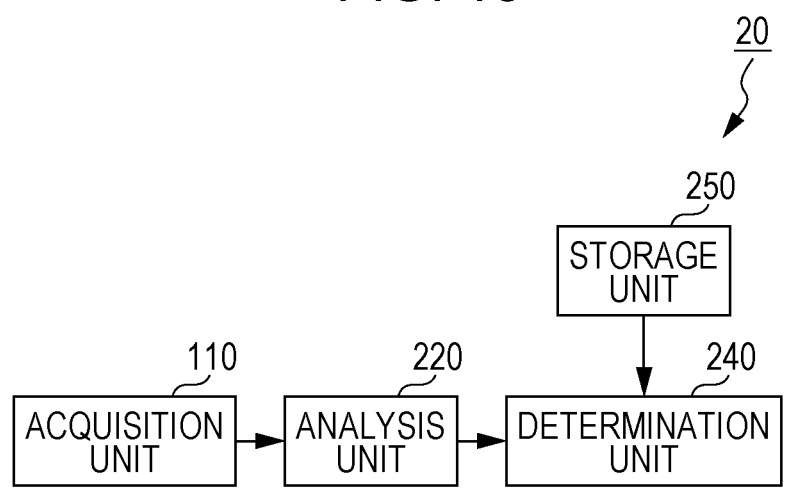
FIG. 10 is a functional block diagram illustrating the configuration of an elapsed-time determination apparatus according to a first modification of the first embodiment.

FIG. 10 is a functional block diagram illustrating the configuration of the elapsed-time determination apparatus 20 according to the first modification of the first embodiment. As illustrated in FIG. 10, the elapsed-time determination apparatus 20 functionally includes the acquisition unit 110, an analysis unit 220, a determination unit 240, and a storage unit 250, as illustrated in FIG. 10. Note that functional components (functional blocks) the same as those of the elapsed-time determination apparatus 10 illustrated in the first embodiment are denoted by the same reference numerals, and detailed description will be omitted here. The analysis unit 220, determination unit 240, and storage unit 250, are the analysis unit 120, determination unit 140, and storage unit 150 illustrated in the first embodiment, that have been partially modified.

The analysis unit 220 is realized by the processor executing the control program, and has the function of detecting the state of the melanophores of the fish, by analyzing the image acquired by the acquisition unit 110. The analysis unit 220 includes the image processing unit 120a and a melanophore state analysis unit 220b. The melanophore state analysis unit 220b has a function of analyzing the state of black portions of the melanophores in the image subjected to processing at the image processing unit 120a. The state of the melanophores in the first modification of the first embodiment is the degree of complexity of the shapes of black portions.

The storage unit 250 is realized by a region of a storage device, and stores correlation information representing the correlation between the state of black portions of melanophores of fish and the amount of time elapsed since the death of the fish, generated beforehand based on experimentation results where change in state of melanophores over time was measured. The correlation information may be a table that stores elapsed time and the state of melanophores, or may store a function of the state of melanophores as to the elapsed time. In the first modification of the first embodiment, the state of melanophores is expressed by the degree of complexity of the shapes of melanophores, and the correlation information represents the correlation where the smaller the complexity in shape of the black portion of a melanophore is, the longer the amount of time elapsed since death.

The determination unit 240 has functions of referencing the correlation information stored in the storage unit 250, judging what state according to time elapsed since death the state of the melanophore analyzed by the melanophore state analysis unit 220b corresponds to, determining the amount of time elapsed since the death of the fish, and outputting the determination results. This determination unit 240 is realized by the processor that executes the control program, and the output device.

The elapsed-time determination processing by the elapsed-time determination apparatus 20 according to the first modification of the first embodiment is generally the same as the elapsed-time determination processing performed by the elapsed-time determination apparatus 10 illustrated in FIG. 4. Accordingly, description of the overview of elapsed-time determination processing will be omitted. Description by the image processing unit 120a of the analysis unit 220 will also be omitted.

Figure 11:
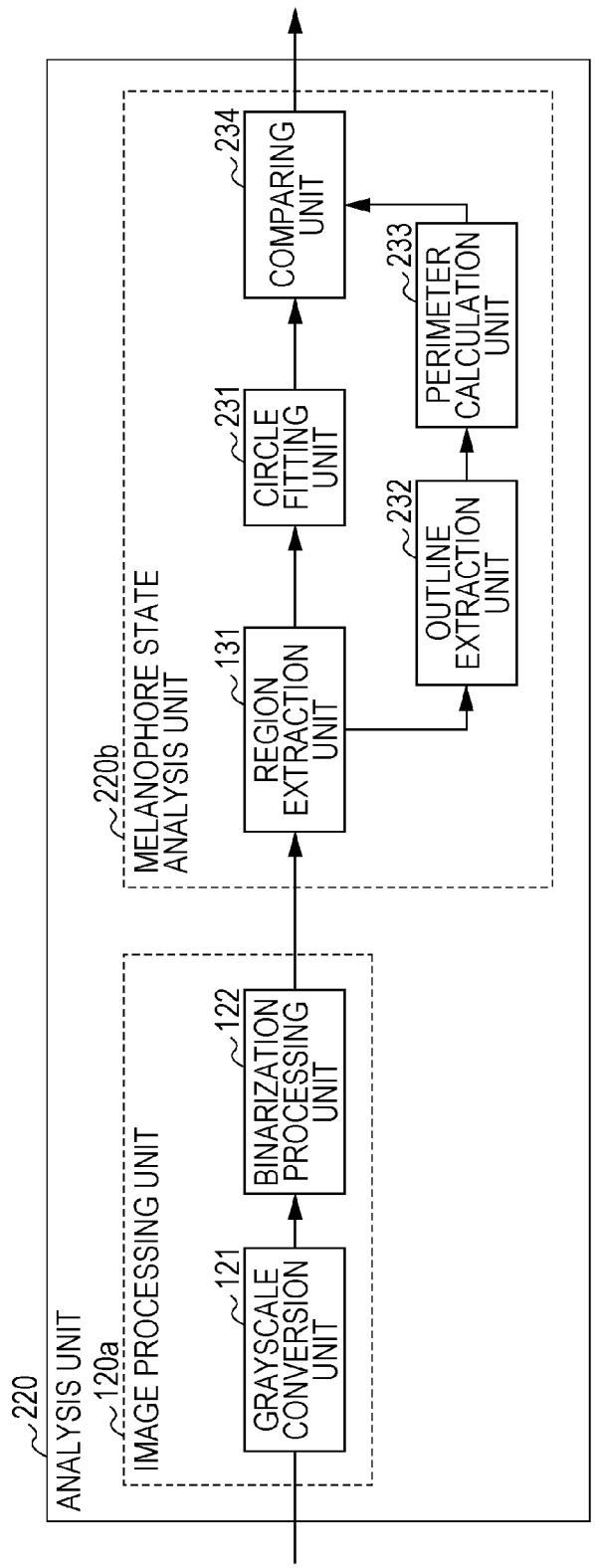
FIG. 11 is a block diagram illustrating an exemplary detailed configuration of an analysis unit according to the first modification of the first embodiment.

The following is a detailed description of the configuration and operations of the melanophore state analysis unit 220b in the analysis unit 220. FIG. 11 is a block diagram illustrating an exemplary detailed configuration of the analysis unit 220. As illustrated in FIG. 11, the analysis unit 120 has the image processing unit 120a and melanophore state analysis unit 220b, and the melanophore state analysis unit 220b includes a region extraction unit 131, a circle fitting unit 231, an outline extraction unit 232, a perimeter calculation unit 233, and a comparing unit 234.

The region extraction unit 131 separates the image binarized at the image processing unit 120a where the back portions have been identified into individual clumps which are clusters of continuous black-portion pixels, and extracts each clump as a black region. The circle fitting unit 231 decides, for each of the one or more black regions extracted by the region extraction unit 131 that have an area equal to or smaller than a predetermined size, a circle of equal area, and calculates the length of the circumference.

The outline extraction unit 232 extracts, for each black region extracted by the region extraction unit 131, an outline, which is a set of pixels making up the boundary between the black region and the white on the outside thereof. The black region here is a clump of consecutive black portions, so a set of pixels making up the boundary between the black region and white region serves as the outline. Outline extraction can be performed using existing contour tracking technology, where the outline is extracted by searching for points of change between white/black in a raster scan (e.g., see "10-2.2 Basic Processing and Measurement of Binary Images (pp. 177-184)" in "Digital Image Processing" by Masatoshi Okutomi (chairman of editorial board), Computer Graphic Arts Society Jul. 22, 2004 (hereinafter simply "Okutomi")).

The perimeter calculation unit 233 calculates the length of the perimeter along the outline of the black region. That is to say, the perimeter calculation unit 233 calculates the entire length of the outline of the black region which the outline extraction unit 232 has extracted. One example of a calculation method is to count the number of pixels making up the outline, i.e., the number of pixels making up the boundary between the black region and white region, and multiple this by the distance per pixel to obtain the total length. Another example is to represent the pixels making up the outline of the black region which the outline extraction unit 232 has extracted, in two-dimensional coordinates in increments of individual pixels, and calculate the distance between each two points for all pixels on the outline, thereby calculating the total distance. Minute changes in the outline due to fine differences in luminance nearby the threshold value at the time of binarizing may be eliminated by running through a low-pass filter at a predetermined spatial frequency when extracting the outline, or performing smoothing of the outline. This enables the perimeter to be calculated by simple calculation. Further, the pixels making up the outline may be thinned out, by leaving one out of every five points or one out of every ten points, for example, thereby simplifying the outline for calculation of the total length thereof. The resolution of the image which the acquisition unit 110 acquires may be higher than the 2 μm (pixel pitch of 2 μm) for calculation of the length of the outline as described above. Although this will differ depending on conditions, such as the type of fish and so forth, the size of a melanophore is around 200 μm to 400 μm, and the arms of the star shape are around 2 μm wide, so the resolution may be higher than 2 μm per pixel.

The comparing unit 234 compares the length of the circumference of the circle having the same area as the black region obtained by the circle fitting unit 231 and the total length of the outline of the black region obtained by the perimeter calculation unit 233.

Deciding the circle by the circle fitting unit 231 will be described below with reference to FIGS. 12A through 12D.

Figure 12A:
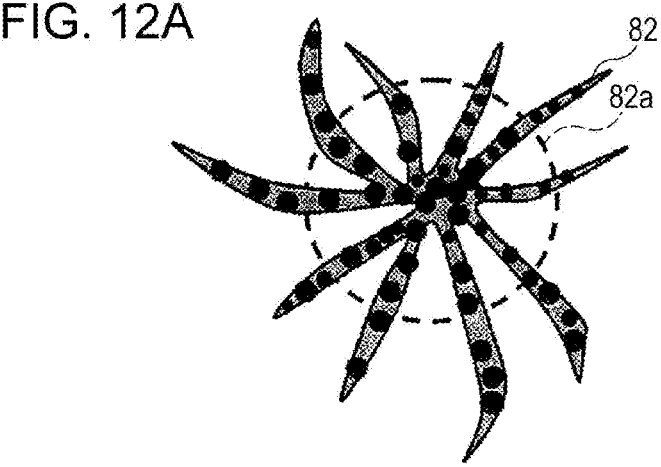
FIG. 12A is a schematic diagram illustrating a circle fitting unit according to the first modification of the first embodiment having decided a circle as to a black region of a melanophore.
Figure 12B:
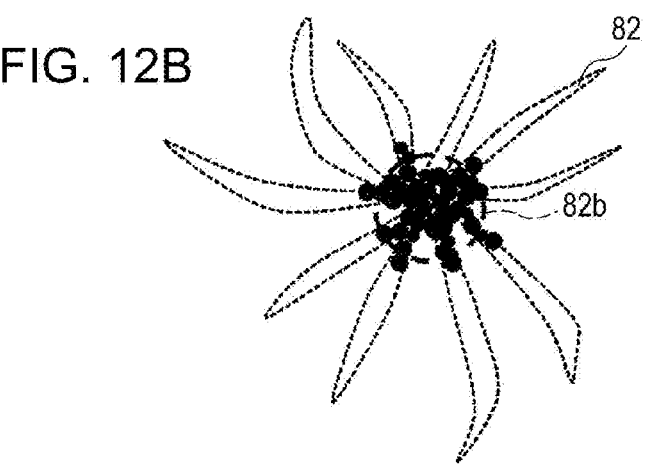
FIG. 12B is a schematic diagram illustrating the circle fitting unit according to the first modification of the first embodiment having decided a circle as to a black region of a melanophore.
Figure 12C:
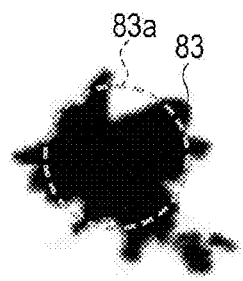
FIG. 12C is a schematic diagram illustrating the circle fitting unit according to the first modification of the first embodiment having decided a circle as to a black region in the image.
Figure 12D:
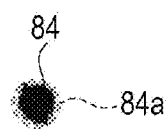
FIG. 12D is a schematic diagram illustrating the circle fitting unit according to the first modification of the first embodiment having decided a circle as to a black region in the image.

FIGS. 12A and 12B are schematic diagrams illustrating the way in which the circle fitting unit 231 decides circles of equal area to a black region of a melanophore. FIG. 12A illustrates the way in which a circle 82a has been decided as to a state where the pigment granules are dispersed throughout the melanophore. FIG. 12B illustrates the way in which a circle 82b has been decided as to a state where the pigment granules are aggregated at the center of the same melanophore as in FIG. 12A. FIG. 12A shows fewer pigment granules than in reality, for the sake of simplicity, but still illustrates that the black region of the melanophore 82 has slender arms forming a star shape, and that the perimeter of the star-shaped black region is longer than the circle 82a that has been decided, so there is ample difference in the lengths of the perimeter and the circumference. FIG. 12B illustrates that the black region of the melanophore 82 has some arms but these arms are short, and there is not as much difference in the lengths of the perimeter of the black region and the circumference of the circle 82b that has been decided as compared to the case in FIG. 12A. FIG. 12C is an enlarged view of the portion encircled by the circle 72a in image 71a, and the way in which a circle 83a of equal area to the black region 83 therein has been decided. FIG. 12D is an enlarged view of the portion encircled by the circle 72f in image 71f, and the way in which a circle 84a of equal area to the black region 84 therein has been decided. While 12C shows that there is ample difference in the length of the perimeter of the black region and the circumference of the circle that has been decided, in FIG. 12D there is no major difference. This degree of difference serves as an index representing the degree of complexity of the shape of the black portion in the melanophore. The comparing unit 234 calculates the degree of difference, and thus compares the length of the perimeter of the black region (total length of the perimeter) with the length of the circumference of the circle having equal area as the black region. Note that deciding the circle by the circle fitting unit 231 is performed to obtain the length of the circumference to be compared at the comparing unit 234, and there is no need to decide the position of the circle or the like.

Figure 13:
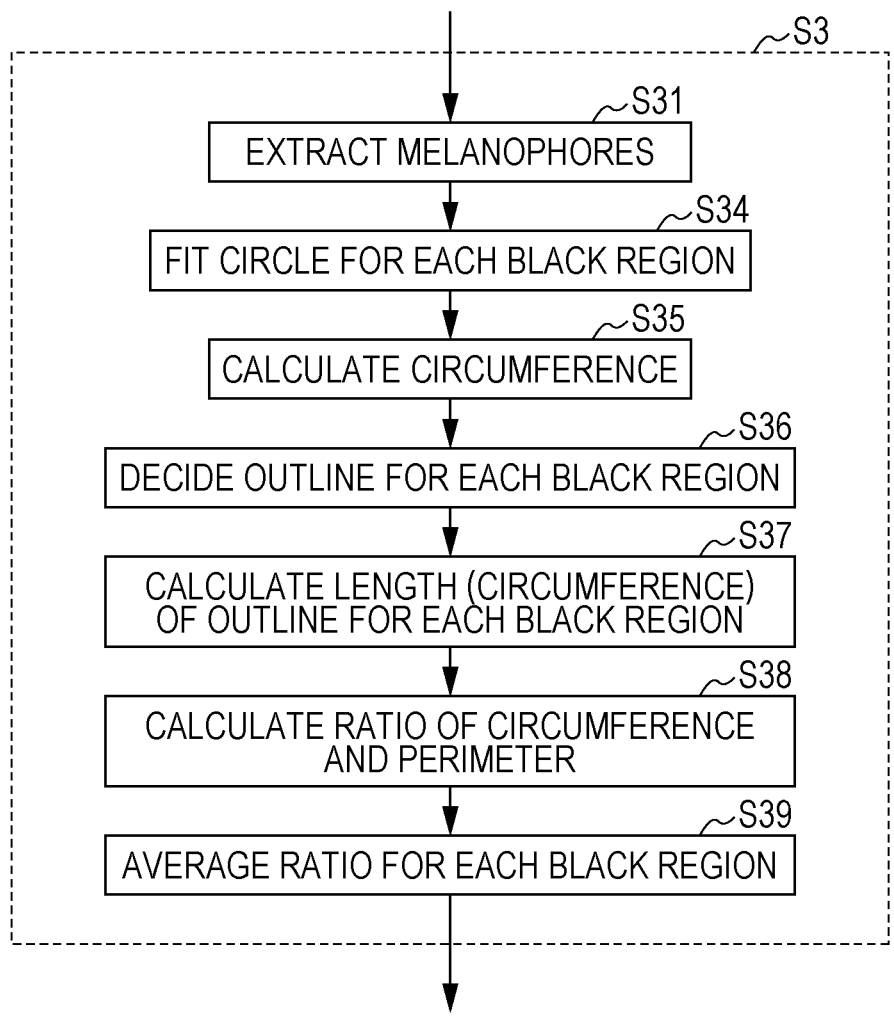
FIG. 13 is a flowchart illustrating a partial detailed example of elapsed-time determination processing according to the first modification of the first embodiment.

FIG. 13 is a flowchart illustrating a partial detailed example of elapsed-time determination processing. Detailed operations of analysis of the melanophore (detection of the state of the melanophore) in step S3 in FIG. 4 will be described with reference to FIG. 13.

The region extraction unit 131 extracts each black region which is the consecutive black portions in the binarized image, as a melanophore (step S31).

The circle fitting unit 231 fits, i.e., decides, a circle of which the area is equal to the black portions of the melanophore extracted in step S31 (step S34). The circle fitting unit 231 further calculates the length of the circumference of the circle fit in step S34 (step S35).

The outline extraction unit 232 decides the outline of the melanophore extracted in step S31 (step S36). The perimeter calculation unit 233 calculates the total length of the outline decided in step S36 (step S37).

The comparing unit 234 calculates the ratio between the length of the perimeter of the black region calculated in step S37 (total length of outline) and the length of the circumference of the circle fit to the black region calculated in step S35 (step S38). The ratio of the length of the perimeter of the back region to the length of the circumference of the circle that has been fit is, for example, a value obtained by dividing the length of the perimeter by the length of the circumference. The ratio of the length of the perimeter of the back region to the length of the circumference of the circle that has been fit represents the degree of difference between the perimeter of the back region and the length of the circumference of the circle that has been fit, and thus serves as an index representing the degree of complexity of the shape of the black portions of the melanophore (i.e., the state of the melanophore). The processing of steps S34 through S38 is performed on each of all melanophores extracted in step S31. The comparing unit 234 then calculates the average of ratios calculated for all of the melanophores (step S39). Thus, the state of the melanophores is detected.

After detection of the state of the melanophores by the analysis described above, the determination unit 240 acquires the average value of the ratios of the perimeters of the black region which is the black portions of the melanophores and the corresponding circumferences of circles, i.e., the complexity of the shape of the black portions of the black regions, calculated in step S39. The determination unit 240 then references the correlation information stored in the storage unit 250, judges what state according to time elapsed since death the state (complexity) of the melanophore analyzed by the melanophore state analysis unit 220b corresponds to, determines the time elapsed since death, and outputs the determination results. Alternatively, step S39 may be omitted, with the determination unit 240 determining the time elapsed since death for each melanophore based on the ratio at each melanophore calculated in step S38 (i.e., the degree of complexity of the shape of the black portions of the melanophore) and the correlation information, and calculate the average of the identified elapsed times. In this case, the averaged elapsed time is the determination value for the amount of time elapsed since the death of the fish. Alternatively, statistical representative values such as median value or the like may be used, instead of using an average value of the degree of complexity of the shape of the black portions of the melanophores, or average value of elapsed time.

Figures 14, 15:
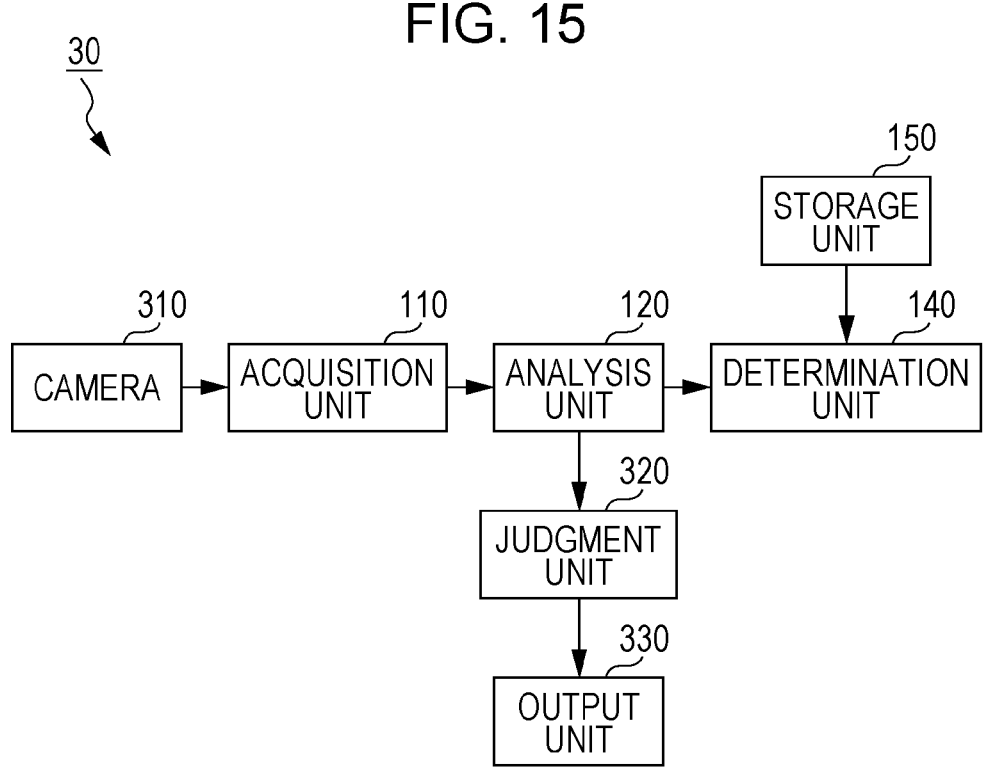
FIG. 14 is a diagram illustrating an example of correlation information stored in a storage unit according to the first modification of the first embodiment.
FIG. 15 is a functional block diagram illustrating the configuration of an elapsed-time determination apparatus according to a second modification of the first embodiment.

FIG. 14 is a diagram illustrating an example of correlation information stored in the storage unit 250. In this example, the correlation between the complexity (state of the melanophore, i.e., complexity of the shape of the black portions of the melanophore) and elapsed time is correlated and stored in the storage unit 250 as a table. The correlation between complexity an elapsed time has been found through experimentation, for example, and elapsed time represents the amount of time elapsed since the death of the fish when preserved at room temperature. The experimentation may have obtained the complexity of shape of the black portions of melanophores on a fish and the amount of time elapsed since the death of the fish when preserved at room temperature from multiple specimens of fish. Note that the storage unit 250 may store correlation information representing the correlation between the complexity of shape of the black portions of melanophores and the amount of time elapsed since the death of the fish in another format instead of storing as the above-described table. For example, the storage unit 250 may store parameters defining functions representing the change in the complexity in shape of the black portions of melanophores over time. The correlation may be stored and referenced in a format other than a table or a function.

The first modification of the first embodiment has been described as using the ratio of the length of the perimeter of the black region (total length of the outline) and the length of the circumference of a circle having the same area as that of the black region, as an index indicating the degree of complexity of the shape of the black portions of the melanophore. Instead of using the ratio, the difference (a value obtained by subtracting the length of the circumference from the length of the perimeter) or the like may be used, as long as the difference between the length of the circumference and the length of the perimeter is represented. Also, instead of using a circle of the same area as the black region, a simple shape such as a regular polygon having the same area as the black region, for example, may be used, in which case the perimeter of the simple shape having the same area as the black region is used instead of the circumference. Alternatively, roundness, which is widely known as a geometric feature parameter in the field of image processing technology, may be used as an index indicating the degree of complexity of the shape of the melanophore. Roundness is obtained as $4\pi S/L2$, where S represents area and L represents perimeter. The maximum roundness value is 1, in a case of a circle, and the smaller the value is, the more complex the shape is. Accordingly, by using an inverse, the greater the value is the more complex the shape is, and this can be used as an index of the degree of complexity. In a case of using roundness as it is as the index, correlation information needs to be stored in the storage unit 250 to the effect that the larger the roundness values is, the longer the time elapsed since death is, and the smaller the roundness values is, the shorter the time elapsed since death is.

Although description has been made above that the elapsed time is at room temperature, the correlation information may represent the correlation between size of black portions of melanophores and elapsed time at each of multiple preservation temperatures, in accordance with the temperatures at which fish to be handled by the elapsed-time determination apparatus 20 are preserved. This may include correlation at refrigeration temperature and ice temperature.

Second Modification of First Embodiment

An elapsed-time determination apparatus 30 according to a second modification of the first embodiment will be described. This elapsed-time determination apparatus 30 has the same hardware configuration as the elapsed-time determination apparatus 10 according to the first embodiment, but the elapsed-time determination apparatus 30 also includes a camera. Due to the control program executed by the processor being different, the following function has been added to the elapsed-time determination apparatus 30.

The elapsed-time determination apparatus 30 according to the second modification of the first embodiments the elapsed-time determination apparatus according to the first embodiment, to which a function of prompting the user to move the camera, so as to acquire images whereby determination of elapsed time can be accurately performed. Acquiring images under conditions where the accuracy of analysis of melanophores is improved enables the accuracy of determination of time elapsed after death to be improved.

FIG. 15 is a block diagram illustrating the configuration of the elapsed-time determination apparatus 30 according to the second modification of the first embodiment. As illustrated in FIG. 15, the elapsed-time determination apparatus 30 functionally includes, in addition to the acquisition unit 110, analysis unit 120, determination unit 140, and storage unit 150 illustrated in FIG. 1, a camera 310, a judgment unit 320, and an output unit 330. Note that functional components (functional blocks) the same as those of the elapsed-time determination apparatus 10 of the first embodiment are denoted by the same reference numerals, and detailed description will be omitted here. Difference as to the elapsed-time determination apparatus 10 will primarily be described here.

The camera 310 shoots a still image of the surface of the fish. The acquisition unit 110 acquires the image from the camera 310. The analysis unit 120 has the function of analyzing the image and detecting the state of the melanophores of the fish, and includes the image processing unit 120a that binarizes the image to extract the black portions of melanophores in the image that has been acquired, and the melanophore state analysis unit 120b that analyzes the state of the black portions of the melanophores.

The judgment unit 320 has a function of determining the distribution state of melanophores within the image, based on the processing results of the image processing unit 120a, and judging whether or not the image acquired from the camera 310 is an image including a part (a portion of the fish) suitable for analysis at the melanophore state analysis unit 120b. This judgment unit 320 is realized by the processor that executes the control program. Whether or not the image includes a part that is suitable for analysis, is judged depending on whether or not a certain range includes a certain percentage of black regions extracted from the image as to the entire image. Specifically, judgment is made based on whether or not the overall average luminance of the image is within a predetermined range that has been determined beforehand. In a range where the maximum value of the average luminesce is 255 for example, and the minimum value is 0 for example, a middle range is decided as the predetermined range, such as 64 to 192, for example. That is to say, this range is set so that the average luminance of images where the amount of black regions extracted as melanophores is so great that analysis is difficult, or so small that the precision of elapsed-time determination will suffer, will not be included in this predetermined range.

The output unit 330 is realized by the output device and the processor that executes the control program, and has a function of displaying a message prompting the user to move the camera, in a case where the camera 310 needs to be moved based on the judgment results of the judgment unit 320. The message is displayed on a display if the output device is a display. The message may be text or images, or audio or printed output. In a case of audio, an audio output device (e.g., a speaker) may be used, and in a case of printing, a printer or the like may be used.

The elapsed-time determination processing performed by the elapsed-time determination apparatus 30 according to the second modification of the first embodiment is a partial modification of the elapsed-time determination processing performed by the elapsed-time determination apparatus 10 illustrated in FIG. 4.

Figure 16:
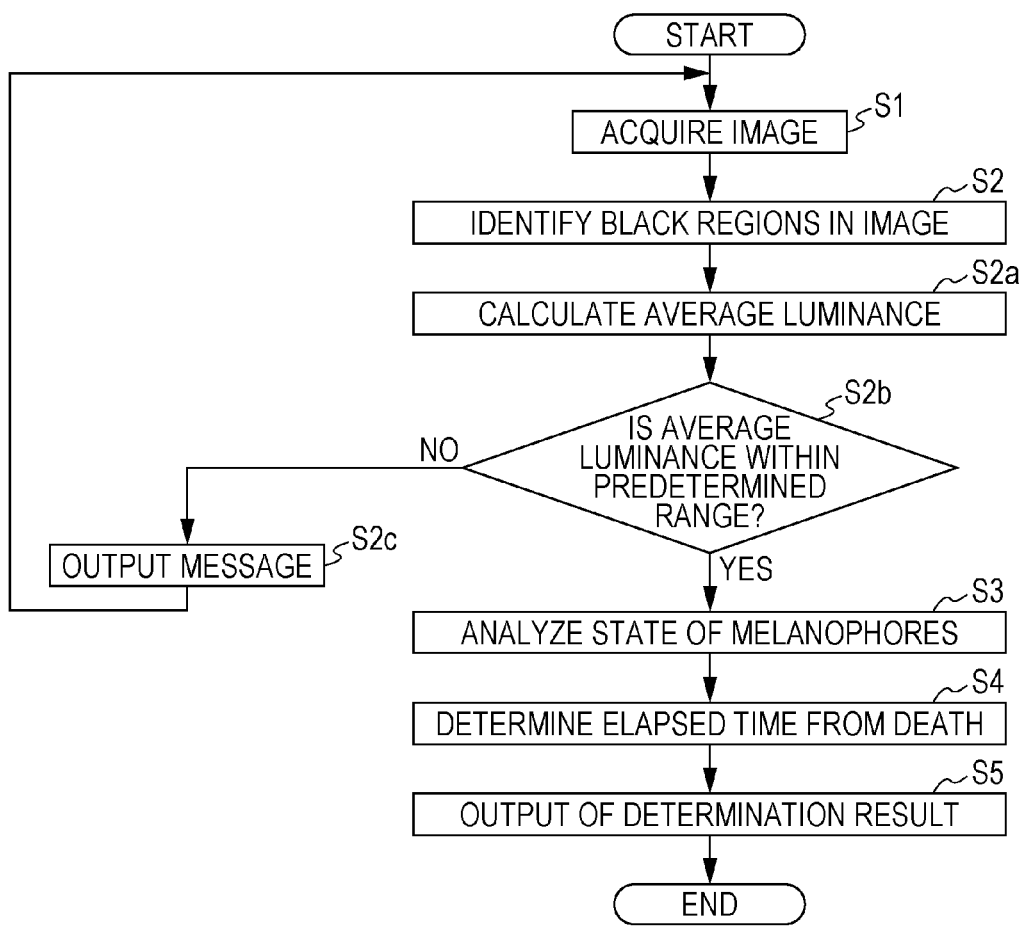
FIG. 16 is a flowchart illustrating elapsed-time determination processing according to the second modification of the first embodiment.

FIG. 16 is a flowchart illustrating the elapsed-time determination processing by the elapsed-time determination apparatus 30. The processing procedures in the elapsed-time determination processing will be described following FIG. 16. This elapsed-time determination processing is started by input to the input unit of the elapsed-time determination apparatus 30 (e.g., by pressing a switch). Note that the elapsed-time determination processing illustrated in FIG. 16 is the elapsed-time determination processing in FIG. 4, to which steps S2a through S2c have been added. Processing procedures the same as those of the elapsed-time determination apparatus 10 are denoted by the same reference numerals, and detailed description thereof will be omitted here.

The acquisition unit 110 acquires a still image taken by the camera 310 (step S1). The image processing unit 120a of the analysis unit 120 identifies black regions in the image by binarizing the image (step S2). The judgment unit 320 calculates the average luminance of the entire image binarized in step S2, thereby obtaining the average luminance (step S2a). Next, the judgment unit 320 determines whether or not the average luminesce obtained in step S2a is within the predetermined range (step S2b). In a case where the average luminesce is found to be within the predetermined range in step S2b, the flow advances to step S3, where the melanophore state analysis unit 120b analyzes the melanophores and detects the state of the melanophores. In a case where the average luminesce is not found to be within the predetermined range in step S2b, the output unit 330 outputs a message prompting the user to move the camera 310 and photograph a different portion of the fish (step S2c). After the processing in step S2c, the user moves the camera 310 and photographs a different portion of the fish, after which the image acquisition in step S1 is executed again. Steps S3 and thereafter are the same as the procedures in the elapsed-time determination apparatus 10.

Thus, in a case where the acquired image of the fish is not suitable for detecting the state of the melanophores to determine elapsed time, the elapsed-time determination apparatus 30 outputs a message to prompt taking of the image again, and accordingly the amount of time elapsed since the death of the fish can be suitably determined.

While description has been made that the judgment unit 320 obtains the average luminance of the image which the image processing unit 120a has binarized, and judges whether or not the average luminesce within the predetermined range, and arrangement may be made where the image before binarization is used to judge whether the image includes a part suitable for analysis. Judgment of whether or not the image includes a part suitable for analysis is judgment regarding whether the amount of melanophores in the image is appropriate. Alternative ways of determining whether the image includes a part suitable for analysis besides average luminesce include using distribution range of luminance, variance, area ratio of white regions and black regions, or the like, as an index, and judging whether to not the index is within a predetermined range set beforehand. That is to say, the image can be judged to be an image including a part suitable for analysis if the ratio of black region extracted from the image, as to the entire image, is included in a certain range at the middle away from the maximum and minimum values.

Second Embodiment

An elapsed-time determination apparatus 40 according to a second embodiment will be described. This elapsed-time determination apparatus 40 has the same hardware configuration as the elapsed-time determination apparatus 10 according to the first embodiment, but the control program executed by the processor is different, and accordingly functions differ somewhat, as follows.

The elapsed-time determination apparatus 10 according to the first embodiment, and the elapsed-time determination apparatus 20 according to the first modification thereof, determine the amount of time elapsed since the death of the fish based on analysis of state of the size (area, etc.) of the melanophores of the fish or of the complexity of the shape of black portions of the melanophores. Conversely, the elapsed-time determination apparatus 40 saves a reference data (prototype) set of time classes. The time classes have been obtained by classifying features (described later) of images of melanophores for each number of elapsed amount of time beforehand, through experimentation and the like. Which reference data the features of the black region extracted from the image of the fish, regarding which the amount of time elapsed since death is to be determined, are closest to in feature space, is decided. The elapsed time corresponding to the decided reference data is then taken as being the amount of time elapsed since the death of the fish.

Figures 17, 18:
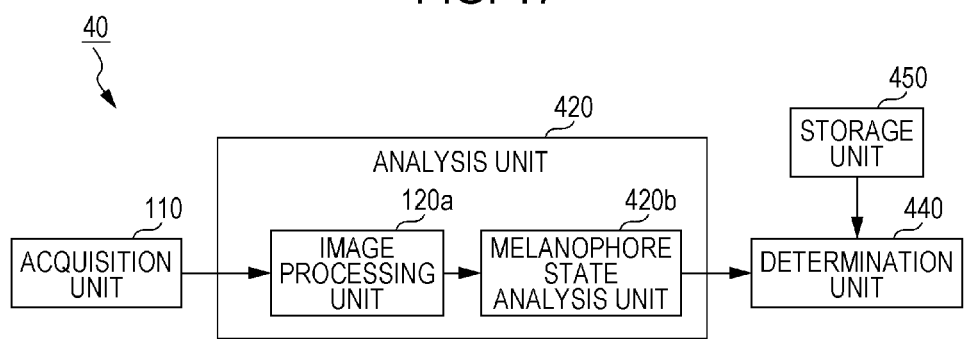
FIG. 17 is a functional block diagram illustrating the configuration of an elapsed-time determination apparatus according to a second embodiment.
FIG. 18 is a diagram exemplarily illustrating reference data sets for each of time classes, which is class information stored in a storage unit according to the second embodiment.

FIG. 17 is a functional block diagram illustrating the configuration of the elapsed-time determination apparatus 40 according to the second embodiment. As illustrated in FIG. 17, the elapsed-time determination apparatus 40 functionally includes the acquisition unit 110, an analysis unit 420, a determination unit 440, and a storage unit 450. Note that functional components (functional blocks) the same as those of the elapsed-time determination apparatus 10 illustrated in the first embodiment are denoted by the same reference numerals, and detailed description will be omitted here. The analysis unit 420, determination unit 440, and storage unit 450, are the analysis unit 120, determination unit 140, and storage unit 150 illustrated in the first embodiment, that have been partially modified.

The analysis unit 420 is realized by the processor that executes the control program. The analysis unit 420 has the function of detecting the state of the melanophores of the fish, by analyzing the image acquired by the acquisition unit 110. The analysis unit 420 includes the image processing unit 120a and a melanophore state analysis unit 420b. The melanophore state analysis unit 420b has a function of analyzing the state of black portions of the melanophores in the image subjected to processing at the image processing unit 120a. The state of black portions in the melanophore is comprehended as features. In a case where there are multiple melanophores in the image, the state is analyzed for each melanophore, and the state of each melanophore is detected. Features are configured as a set of features obtained by image analysis regarding black portions of melanophores, such as for example, roundness, bounding box, area, perimeter, and so forth. Roundness here is how close the shape of black portions of a melanophore is to a circle, and a bounding box is a smallest rectangle circumscribing black portions of a melanophore. Perimeter is the amount of movement necessary to travel around the outline of a region made up of the black portions of a melanophore.

The storage unit 450 is realized by a region of a storage device, and stores class information that is a reference data set of time classes where features have been classified, generated beforehand based on experimentation results of having measure the change in features of the images of melanophores over time, for each number of elapsed hours. This class information is equally significant with the correlation information in the first embodiment. The state of melanophores in the class information serving as the correlation information here is expressed in terms of features including the area of the black portions of melanophores and the degree of complexity of the shapes of black portions, for example. The reference data set of time classes is created beforehand by statistical learning, using image data of melanophores of a great number of fish regarding which the amount of time elapsed since death is known, through experimentation. Existing technology is used as the method for creating the reference data set, as follows (e.g., see "13-1 Pattern Recognition in Image Processing (pp. 220-223)", Okutomi). First, images of melanophores of a fish, regarding which the amount of time elapsed since death is known, are binarized in the same way as with the image processing unit 120a for example, and features (e.g., roundness, bounding box, area, and perimeter) are measured for each. The features are expressed as feature vectors. Time classes are then created in feature space made up of the feature vectors, for each elapsed amount of time (each section of multiple sections into which elapsed time is sectioned) after death, corresponding to the melanophores. The center of gravity in the feature space of one or more features of the melanophores belonging to that class is taken as reference data (prototype). While the features illustrated here are features relating to a partial shape of the image, features are not restricted to shapes. If other features such as color information and so forth can be used in a case where image binarization is not performed for example, features such as color, luminance, and so forth may be used as features. FIG. 18 is a diagram exemplarily illustrating reference data sets for each of time classes, which is class information stored in the storage unit 450. In each time class, elapsed time since death corresponds to the features on the image of the melanophores of the fish in that time class.

The determination unit 440 is realized by the processor that executes the control program, and the output device. The determination unit 440 has functions of referencing the class information (i.e., correlation information) stored in the storage unit 450, determining the amount of time elapsed since the death of the fish by judging the reference data close to the state of the melanophore analyzed by the melanophore state analysis unit 420b, for each melanophore, and outputting the determination results. Note that the determination unit 440 judges which reference data feature vector of the time classes the features (feature vector) of the melanophore is the closest to in feature space, and determines the amount of time elapsed since the death of the fish as a comprehensive determination based on the elapsed time according to the closest reference data.

Figure 19:
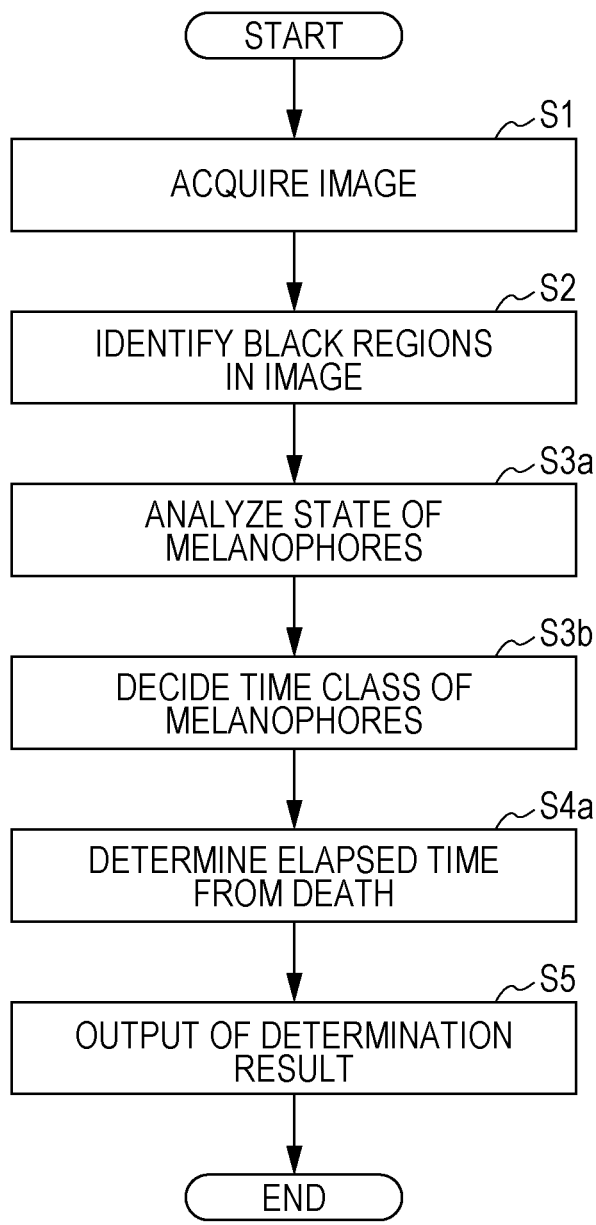
FIG. 19 is a flowchart illustrating elapsed-time determination processing according to the second embodiment.

FIG. 19 is a flowchart illustrating elapsed-time determination processing by the elapsed-time determination apparatus 40 according to the second embodiment. The processing procedures in the elapsed-time determination processing performed by the elapsed-time determination apparatus 40 will be described following FIG. 19. This elapsed-time determination processing is started by input to the input unit of the elapsed-time determination apparatus 40 (e.g., by pressing a switch or the like).

First, the acquisition unit 110 of the elapsed-time determination apparatus 40 acquires a still image from the acquisition device (step S1). The image processing unit 120a of the analysis unit 420 identifies black regions in the image by performing image processing on the acquired image (step S2). Next, the melanophore state analysis unit 420b of the analysis unit 420 extracts melanophores from the black regions identified in step S2, and detects the state of the melanophores by analyzing the melanophores (step S3a). The features in the image are used as the state of the melanophores.

Next, the determination unit 440 references the class information stored in the storage unit 450, based on the state (features) of the melanophores detected by the analysis unit 420 in step S3a, and decides a time class of reference data the closest to the features in the feature space (step S3b). The determination unit 440 determines the amount of time elapsed since the death of the fish as a comprehends determination time class decided for each melanophore (step S4a), and outputs the determination results (step S5). In step S4a, the most frequent value (or mode) of all elapsed times corresponding to all time classes decided in step S3b, for example, is determined to be the amount of time elapsed since the death of the fish.

Thus, the elapsed-time determination apparatus 40 analyzes the state of melanophores from an image of a fish that has been acquired, and determines the amount of time elapsed since the death of the fish by fitting into models representing features of melanophores on the image at each predetermined elapsed time.

In the second embodiment, the determination unit 440 determines, out of multiple elapsed times decided for multiple melanophores, the elapsed time corresponding to a time class which appears most frequently, as being the amount of time elapsed since the death of the fish. Instead of the elapsed time corresponding to the time class which appears most frequently, the average or median value or the like of the multiple elapsed times decided for multiple melanophores may be employed as the amount of time elapsed since the death of the fish. Also, while the storage unit 450 has been described as storing the elapsed time corresponding to a time class as a unique value, a range of elapsed time may be stored for each time class. In this case, in step S4a, the range of elapsed time corresponding to each in the reference data set may partially overlap. In this case, an elapsed time obtained by weighted averaging of all elapsed time ranges corresponding to all time classes decided in step S3b can be determined to be the amount of time elapsed since the death of the fish.

Third Embodiment

There are both fresh fish and frozen fish circulating as edible fish on the market. While the market value of the same type of fish will differ depending on whether fresh or frozen, advances in freezing and thawing technology has made it more difficult to tell the difference between fresh fish and frozen fish. Being able to easily tell whether a fish has been preserved by freezing or is a fresh fish that has been preserved without freezing is useful for both common consumers and during distribution. In a third embodiment, a preservation state determination apparatus 50 will be described, which determines the preservation state of fish, such as whether a fish has been preserved by freezing or not. Determination of the preservation state of the fish is realized by comparing the actual amount of time elapsed since the death of the fish that has been input, and the amount of time elapsed since the death of the fish determined from the state of melanophores analyzed from an image of melanophores in an iris or fin of the fish.

Before describing the third embodiment in detail, description will be made regarding the state of melanophores after preservation by freezing, that the present Inventors have discovered. The present inventors froze a fish (Japanese dace) one hour after death at −80° C. or lower, thawed the Japanese dace that had been preserved by freezing for one day or more at −80° C. or lower, and observed change in the melanophores after freezing.

Figure 20:
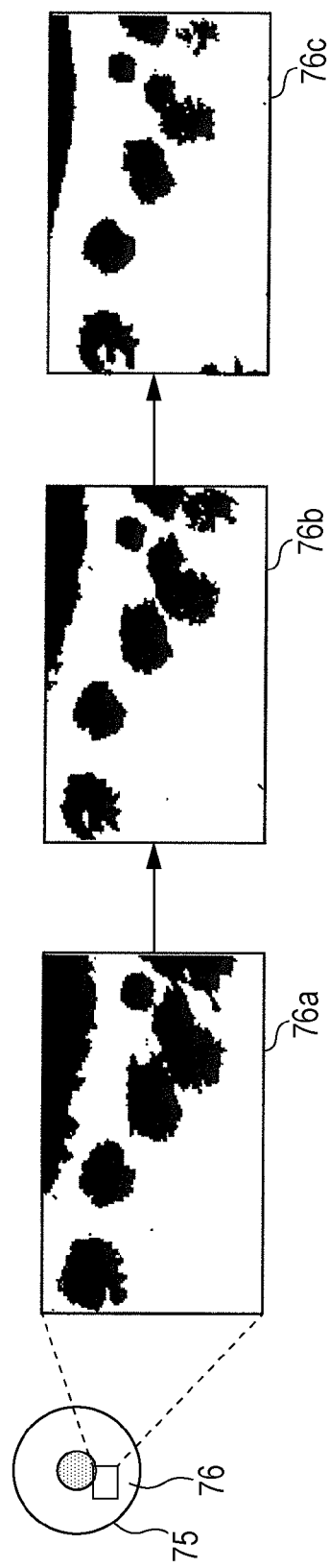
FIG. 20 is a diagram illustrating binary images of an iris of a fish.

FIG. 20 illustrates a group of images, taken of a portion of a frozen Japanese dace, allowed to thaw naturally, including an iris 76 of an eye 75, magnified approximately 200 times. The images 76a through 76c are images shot immediately after thawing (0 hours elapsed), four hours elapsed after thawing, and eight hours elapsed after thawing, respectively. These images have been binarized, in the same way as FIG. 1. The black portion at the upper right in each image is the iris. Although FIG. 1 exhibited great change in the state of the melanophores over time, the frozen fish illustrated in FIG. 20 exhibits lithe change in the state of the melanophores regardless of time elapsing after having been thawed. That is to say, even after eight hours after thawing, the pigment granules of the melanophores of the frozen fish are spread following the complex shape of the cell of the melanophore with many protrusions, so the black portions form a complex shape with many protrusions, and also the black pigment granules are spread over a wide area.

Based on the above-described discovery, a preservation state determination apparatus will be described in the third embodiment, which acquires images of irises or fins of fish, determines the amount of time elapsed since the death of the fish by analyzing the images, and determines the preservation state of the fish based on the determination results.

The preservation state determination apparatus 50 is configured including an input unit, a storage device which is memory for example, an image acquisition unit which is an imaging sensor of a camera for example, an output device which is a display for example, and a computer having a processor for example, in the same way as the elapsed-time determination apparatus 10 described in the first embodiment. The memory stores a control program for causing the processor to execute preservation state determination processing, for example, and is used to store data and the like used by the processor at the time of executing the preservation state determination processing.

The preservation state determination apparatus 50 has the function of executing the preservation state determination processing according to the preservation state determination method. By way of the same components as the elapsed-time determination apparatus 10, the preservation state determination apparatus 50 has the function of determining the amount of time elapsed since the death of a fish, based on the state of the melanophores of the first from the acquired image of the fish, and from these determination results, further determining the preservation state of the fish. That is to say, the preservation state determination apparatus 50 extracts the melanophores of the first from an acquired image of the fish, calculates the area of the black portions thereof, determines the amount of time elapsed since the death of the fish based on the area, and determines whether or not the fish has been preserved by freezing from the elapsed time.

Figure 21:
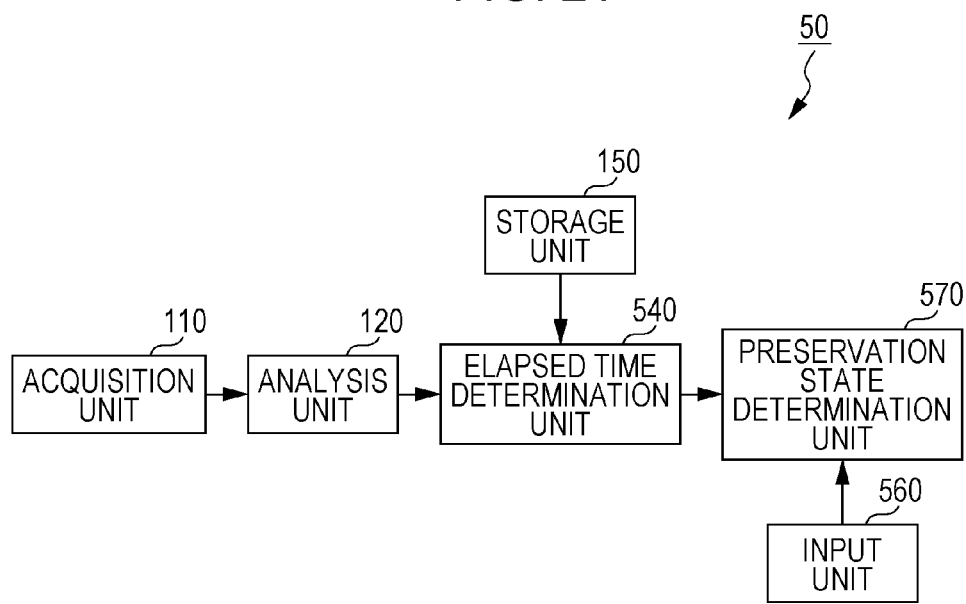
FIG. 21 is a functional block diagram illustrating the configuration of a preservation state determination apparatus according to a third embodiment.

FIG. 21 is a functional block diagram illustrating the configuration of the preservation state determination apparatus 50 according to the third embodiment. The preservation state determination apparatus 50 functionally includes the acquisition unit 110, analysis unit 120, an elapsed time determination unit 540, the storage unit 150, an input unit 560, and a preservation state determination unit 570, as illustrated in FIG. 21. Note that functional components (functional blocks) the same as those of the elapsed-time determination apparatus 10 illustrated in the first embodiment are denoted by the same reference numerals, and detailed description will be omitted here.

The elapsed time determination unit 540 is equivalent to the determination unit 140 described in the first embodiment, but the output destination of the determination results thereof is the preservation state determination unit 570, with the elapsed time determined by the elapsed time determination unit 540 being transmitted to the preservation state determination unit 570. Note that the correlation information stored in the storage unit 150 relates to the amount of time elapsed since death at room temperature, and the amount of time elapsed since the death of the fish that the elapsed time determination unit 540 determines is the amount of time elapsed since death at room temperature.

The input unit 560 is realized by an input device or the like to acquire information externally, and has a function of accepting input of information indicating the amount of time elapsed since the death of a fish relating to an image acquired by the acquisition unit 110, and transmit the amount of time elapsed since death to the preservation state determination unit 570. For example, if the input device is a keyboard, input of information indicating the amount of time elapsed since death can be accepted from the user. Alternatively, radio frequency identifier (RFID) technology may be used to accept input by a tag reader device reading information from an integrated circuit (IC) tag attached to the fish itself, or packaging or a box used to preserve or ship the fish, that is capable of output of information indicating the amount of time elapsed since death of the fish. Also, input of information indicating the amount of time elapsed since death may be received and accepted from other terminal devices. Reception of this information is realized by cabled communication, wireless communication, infrared communication, and so forth. Information indicating the amount of time elapsed since death may be direct information of the amount of time elapsed, or may be indirect information of the amount of time elapsed, such as the date and time of landing the catch, the date and time of packaging, location of landing and form of shipping, or the like. In a case where the information indicating the time elapsed since death that has been received is information indirectly indicating the time elapsed such as the date and time of landing the catch, for example, the input unit 560 may identify the time elapsed since death using the current date and time or the like, and notify this to the preservation state determination unit 570.

The preservation state determination unit 570 has the functions of determining the preservation state of the fish by comparing the time elapsed since death that has been determined by the elapsed time determination unit 540 based on the state of melanophores of the fish, and the time elapsed since death acquired from the input unit 560, and outputting the determination results. Specifically, in a case where the time elapsed since death determined by the elapsed time determination unit 540 is shorter than the time elapsed since death according to the input accepted by the input unit 560, for example, the preservation state determination unit 570 determines that the fish has been preserved by freezing at some stage. A condition to determine that the first has been preserved by freezing at some stage may include that the difference between the determined time elapsed since death and the input time elapsed since death exceeds a predetermined level. This predetermined level may be one hour or the like, for example, and is set beforehand taking margin of error into consideration.

Figure 22:
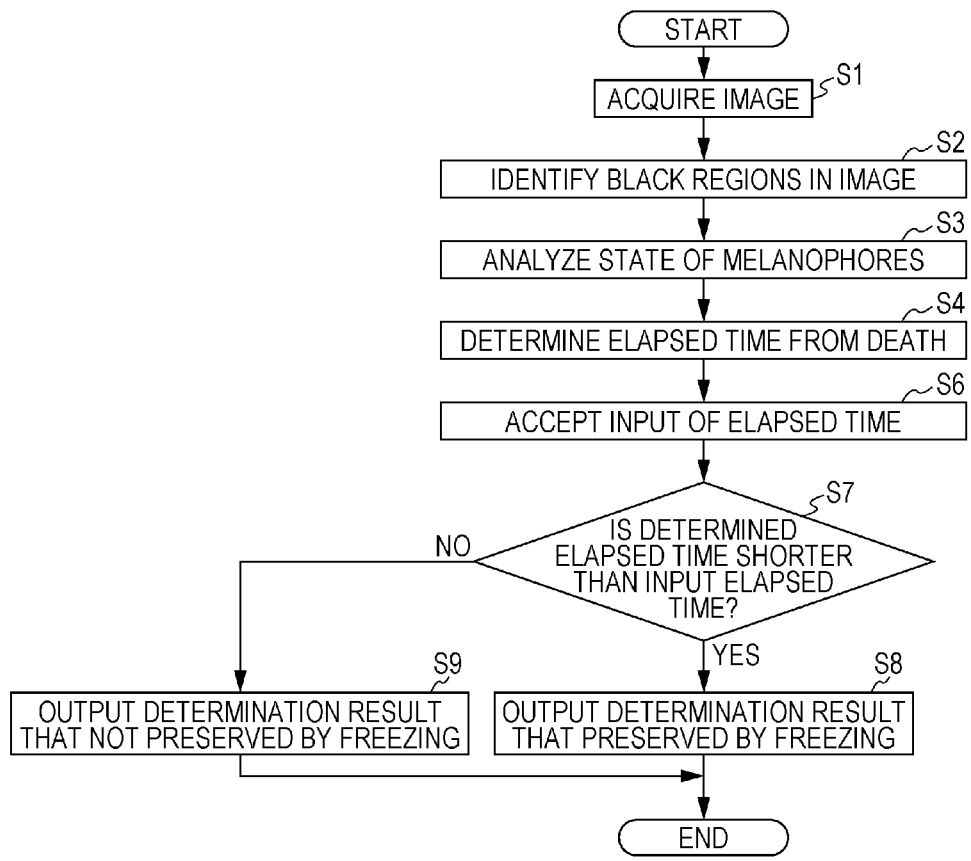
FIG. 22 is a flowchart illustrating preservation state determination processing according to the third embodiment.

FIG. 22 is a flowchart illustrating the preservation state determination processing by the preservation state determination apparatus 50 according to the present embodiment. The processing procedures in the preservation state determination processing will be described following FIG. 22. This preservation state determination processing is started by input to the input unit of the preservation state determination apparatus 50 (e.g., by pressing a switch or the like). The preservation state determination processing includes the procedures of steps S1 through S4 in the elapsed-time determination processing described in the first embodiment.

First, the acquisition unit 110 of the preservation state determination apparatus 50 acquires a still image from the acquisition device (step S1). This image has been taken so as to include an iris or fin of the fish. The image processing unit 120a of the analysis unit 120 identifies black regions in the image by performing image processing on the acquired image (step S2). Next, the melanophore state analysis unit 120b of the analysis unit 120 extracts melanophores from the black regions identified in step S2, and detects the state of the melanophores by analyzing the melanophores (step S3). Next, the elapsed time determination unit 540 determines the amount of time elapsed since the death of the fish by referencing the correlation information stored in the storage unit 150 (step S4), based on the state of the black region detected by the analysis unit 120 (melanophore state analysis unit 120b) in step S3. The elapsed time determination unit 540 transmits the determined elapsed time to the preservation state determination unit 570.

The input unit 560 accepts input of information indicating the amount of time elapsed since the death of the fish, and transmits the time elapsed since death to the preservation state determination unit 570 based on the input (step S6).

The preservation state determination unit 570 compares the elapsed time determined by the elapsed time determination unit 540 based on the state of melanophores of the fish, and the amount of time elapsed since the death of the fish based on the input received from the input unit 560, and judges whether the determined elapsed time is shorter than the elapsed time based on input (step S7). In a case where judgment is made that the determined elapsed time is shorter than the elapsed time based on input, the preservation state determination unit 570 determines that the fish has been preserved by freezing, and outputs determination results accordingly (step S8). In a case where judgment is made that the determined elapsed time is not shorter than the elapsed time based on input, the preservation state determination unit 570 determines that the fish has not been preserved by freezing, and outputs determination results accordingly (step S9). The output in steps S8 and S9 is display of text, images, or the like, if the output device is a display. The output may be audio or printed output instead. In a case of audio, an audio output device (e.g., a speaker) may be used as the output device. In a case of printing output, a printer or the like may be used as the output device.

While description has been made in the third embodiment that the correlation information stored in the storage unit 150 relates to elapsed time after death at room temperature, this may be information relating to elapsed time after death in a preservation state at non-freezing temperatures other than room temperature (e.g., refrigeration temperature, ice temperature, etc.). This will be described in detail later.

Although description has been made in the third embodiment that the determination of whether the fish has been preserved by freezing is made by judging whether or not the elapsed time determined from the state of melanophores is shorter than the elapsed time based on input, alternatively, the determination of whether the fish has been preserved by freezing may be made by judging whether or not the elapsed time determined from the state of melanophores agrees with the elapsed time based on input. If the two do not agree, determination is made that the fish has been preserved by freezing. In this case also, the judgment of not matching may be made in a case where the difference between the elapsed time determined from the state of melanophores and the elapsed time based on input exceeds a certain level, taking margin of error into consideration. Further, three states may be distinguished, namely, a case where the determined elapsed time is shorter than the elapsed time based on input, a case where the determined elapsed time agrees with the elapsed time based on input, and a case where the determined elapsed time is longer than the elapsed time based on input. For example, in a case where the correlation information stored in the storage unit 150 represents the time elapsed since death at refrigeration temperature or ice temperature, determination can be made that if the determined elapsed time is shorter than the elapsed time based on input, the fish has been preserved by freezing. If the determined elapsed time agrees with the elapsed time based on input, the fish has been preserved at that refrigeration temperature or ice temperature, and if the determined elapsed time is longer than the elapsed time based on input, the fish has been preserved at a higher temperature than the refrigeration temperature or ice temperature (e.g., room temperature).

Thus, the preservation state determination apparatus 50 can determine the preservation state of the fish by comparing the time elapsed since death of the fish determined by analyzing the state of melanophores of the fish from an acquired image of the fish, and the time elapsed since death of the fish acquired otherwise. Thus, the user of the preservation state determination apparatus 50 can know whether a fish that appears to be fresh actually is fresh, or has been frozen at one point (i.e., a thawed frozen fish).

Although the third embodiment has been described as using the area of melanophores in the same way as the first embodiment, as a method to determine the elapsed time since death from the image of melanophores that has been acquired, this is not restrictive. The shape, and particularly complexity, of the melanophores may be used, as described in the first modification of the first embodiment, or features of the melanophores may be used to determine the elapsed time since death as described in the second embodiment. Moreover, a function to prompt the user to move the camera in a case where the ratio of melanophores in the image is not within a predetermined range may be provided as described in the second modification of the first embodiment, in order to obtain an image where the melanophores are easily extracted.

First Modification of Third Embodiment

In the third embodiment, description has been made regarding the preservation state determination apparatus 50 having the storage unit 150 storing correlation information relating to the amount of time elapsed since the death of the fish at room temperature. A preservation state determination apparatus 50a will be described as a first modification of the third embodiment, having a storage unit 550 storing correlation information relating to the amount of time elapsed since the death of the fish at multiple temperatures in a non-freezing temperature range, thereby determining the preservation state of the fish. This preservation state determination apparatus 50a has the same hardware configuration as the preservation state determination apparatus 50 according to the third embodiment, but the control program executed by the processor is different, and accordingly functions differ.

Figure 23:
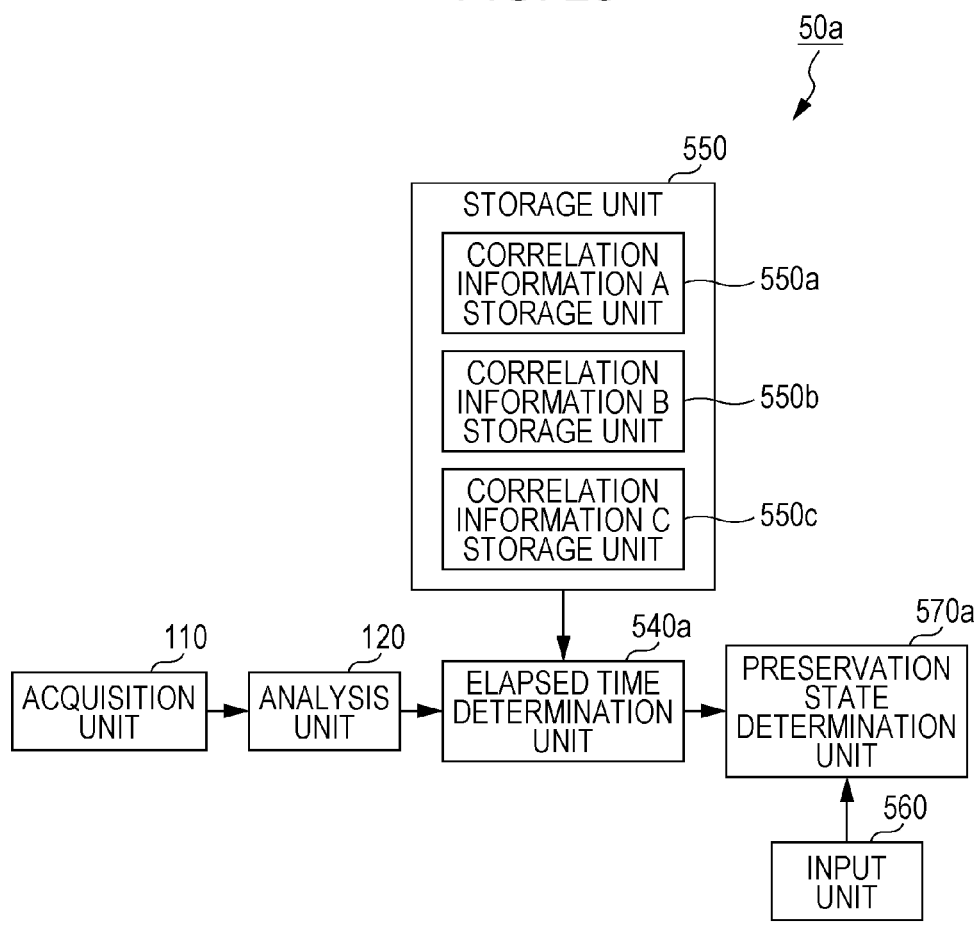
FIG. 23 is a functional block diagram illustrating the configuration of a preservation state determination unit according to a first modification of the third embodiment.

FIG. 23 is a functional block diagram illustrating the configuration of the preservation state determination apparatus 50a according to the first modification of the third embodiment. The preservation state determination apparatus 50a functionally includes the acquisition unit 110, the analysis unit 120, an elapsed time determination unit 540a, the storage unit 550, an input unit 560, and a preservation state determination unit 570a, as illustrated in FIG. 23. Functional components (functional blocks) the same as those in the preservation state determination apparatus 50 illustrated in the third embodiment are denoted with the same reference numerals, and detailed description will be omitted here. The elapsed time determination unit 540a is a partial modification of the elapsed time determination unit 540 illustrated in the third embodiment, and the preservation state determination unit 570a is a partial modification of the preservation state determination unit 570 illustrated in the third embodiment.

The storage unit 550 is realized by a region of a storage device such as memory or the like, and stores multiple sets of correlation information (correlation information A through C) representing the correlation between the state of black portions of melanophores of fish and the amount of time elapsed since the death of the fish, generated beforehand based on experimentation results of measurement of change in the state of melanophores over time. The storage unit 550 includes a correlation information A storage unit 550a, a correlation information B storage unit 550b, and a correlation information C storage unit 550c, which are storage region corresponding to the correlation information A through C, respectively.

The correlation information A storage unit 550a stores the correlation information A that represents the correlation information between the state of the black portions of the melanophores of a fish and the amount of time elapsed since the death of the fish, generated beforehand based on experimentation results where the change in the state of melanophores were measured over time in a case where the first is preserved at room temperature. The correlation information A may be decided based on experimentation results where the state of melanophores in the fish (e.g., the average area of melanophores or the complexity of shape of melanophores) and the amount of time elapsed since death at room temperature is obtained from multiple fish. Note that while the term "room temperature" generally refers to a temperature around 20° C., this may be set to a range of 15° C. to 25° C.

The correlation information B storage unit 550b stores the correlation information B that represents the correlation information between the state of the black portions of the melanophores of a fish and the amount of time elapsed since the death of the fish, generated beforehand based on experimentation results where the change in the state of melanophores were measured over time in a case where the first is preserved by refrigeration (i.e., a case where the fish is preserved at a refrigeration temperature around 5° C.). The correlation information B may be decided based on experimentation results where the state of melanophores in the fish (e.g., the average area of melanophores or the complexity of shape of melanophores) and the amount of time elapsed since death at refrigeration temperature is obtained from multiple fish.

The correlation information C storage unit 550c stores the correlation information C that represents the correlation information between the state of the black portions of the melanophores of a fish and the amount of time elapsed since the death of the fish, generated beforehand based on experimentation results where the change in the state of melanophores were measured over time in a case where the first is preserved at ice temperature (i.e., a case where the fish is preserved at the temperature of ice, around 0° C.). The correlation information C may be decided based on experimentation results where the state of melanophores in the fish (e.g., the average area of melanophores or the complexity of shape of melanophores) and the amount of time elapsed since death at ice temperature is obtained from multiple fish. Note that the definition of "preservation by freezing" is a case where a fish, which has been frozen at −18° C. or lower, is preserved at −18° C. or lower.

FIG. 24 is a diagram exemplarily illustrating an example of correlation information A through C stored in the storage unit 550 (correlation information A storage unit 550a, correlation information B storage unit 550b, and correlation information C storage unit 550c), each stored as tables correlating the average area of melanophores and elapsed time. An example where the correlation information A through C are stored as tables illustrating correlation between the average area of melanophores and the amount of time elapsed. The correlation information A illustrates the correlation between the average area of melanophores and the amount of time elapsed since the death of the fish in the case of having preserved the fish at room temperature, and is the same as the correlation information stored in the storage unit 150 in the first embodiment (see FIG. 8).

The correlation information B illustrates the correlation between the average area of melanophores and the amount of time elapsed since the death of the fish in the case of having preserved the fish at refrigeration temperature. The correlation information B in FIG. 24 illustrates that the amount of time elapsed since the death of the fish until reaching the same average area of melanophores as the correlation information A is longer, meaning that the change in the melanophores is slower for preservation by refrigeration as compared to preservation at room temperature (i.e., the rate of change is smaller). The correlation information C illustrates the correlation between the average area of melanophores and the amount of time elapsed since the death of the fish in the case of having preserved the fish at ice temperature. The correlation information C and correlation information B in FIG. 24 illustrate the change of the melanophores is even slower for preservation at ice temperature as compared to preservation by refrigeration.

The correlation information A may be decided based on experimentation results where the average area of melanophores in the fish and the amount of time elapsed since death at room temperature is obtained from multiple fish. The correlation information B may be decided based on experimentation results where the average area of melanophores in the fish and the amount of time elapsed since death at refrigeration temperature is obtained from multiple fish. The correlation information C may be decided based on experimentation results where the average area of melanophores in the fish and the amount of time elapsed since death at ice temperature is obtained from multiple fish.

The elapsed time determination unit 540a has functions of referencing the correlation information stored in each of the correlation information A storage unit 550a, correlation information B storage unit 550b, and correlation information C storage unit 550c (correlation information A through C) in the storage unit 550, judging what state according to time elapsed since death at room temperature the state of the melanophores analyzed by the analysis unit 120 corresponds to, determining the elapsed time since death, and output the determination results. The elapsed time determination unit 540a is realized by the processor or the like executing the control program. The elapsed time determination unit 540a determines the amount of time elapsed since the death of the fish in each of the cases of preservation at room temperature, preservation by refrigeration temperature, and preservation at ice temperature.

The preservation state determination unit 570a has functions of comparing the amount of time elapsed regarding preservation at each of the temperatures since the death of the fish, determined by the elapsed time determination unit 540a based on the state of the melanophores of the fish, and the amount of time elapsed since death acquired from the input unit 560, thereby determining the preservation state of the fish, and output the determination results.

Figure 25:
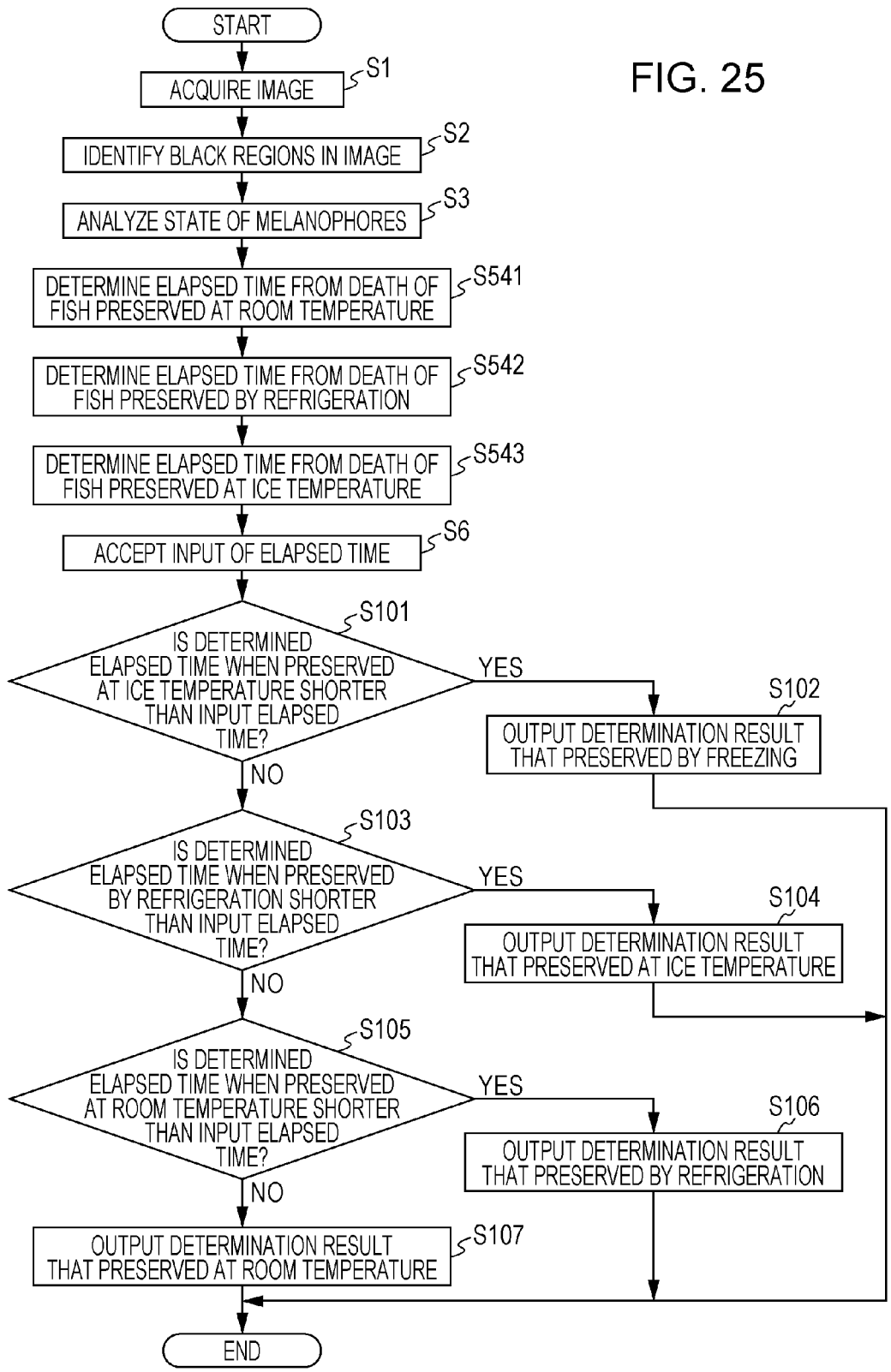
FIG. 25 is a flowchart illustrating preservation state determination processing according to the first modification of the third embodiment.

FIG. 25 is a flowchart illustrating preservation state determination processing by the preservation state determination apparatus 50a according to the first modification of the third embodiment. The processing procedures of the preservation state determination processing will be described following FIG. 25. Note that the preservation state determination processing also includes the procedures of steps S1 through S3 in the elapsed-time determination processing illustrated in the first embodiment.

First, the acquisition unit 110 of the preservation state determination apparatus 50a acquires a still image from the acquisition device (step S1). This image includes an iris or fin of the fish. The image processing unit 120a of the analysis unit 120 identifies black regions in the image by performing image processing on the acquired image (step S2). Next, the melanophore state analysis unit 120b of the analysis unit 120 extracts melanophores from the black regions identified in step S2, and detects the state of the melanophores by analyzing the melanophores (step S3). The average area of the melanophores is obtained here.

Next, the elapsed time determination unit 540a references the correlation information A stored in the correlation information A storage unit 550a, and determines the amount of time elapsed since the death of the fish in a case of preservation at room temperature (step S541), based on the state of black regions (average area of the melanophores here) detected by the analysis unit 120 (melanophore state analysis unit 120b) in step S3. The elapsed time determination unit 540a also references the correlation information B stored in the correlation information B storage unit 550b, and determines the amount of time elapsed since the death of the fish in a case of preservation at refrigeration temperature (step S542), based on the state of black regions detected by the analysis unit 120 (melanophore state analysis unit 120b) in step S3. Further, the elapsed time determination unit 540a references the correlation information C stored in the correlation information C storage unit 550c, and determines the amount of time elapsed since the death of the fish in a case of preservation at ice temperature (step S543), based on the state of black regions detected by the analysis unit 120 (melanophore state analysis unit 120b) in step S3. The elapsed time determination unit 540a then transmits the determination results regarding the amount of time elapsed since the death of the fish in each case of preservation at the different temperatures, to the preservation state determination unit 570a.

The input unit 560 accepts input of information indicating the amount of time elapsed since the death of the fish, and transmits the time elapsed relating to the accepted input to the preservation state determination unit 570a (step S6).

The preservation state determination unit 570a compares the elapsed time at ice temperature determined by the elapsed time determination unit 540a referencing the correlation information C based on the state of the melanophores of the fish, with the elapsed time according to the input acquired from the input unit 560, and judges whether or not the determined elapsed time at ice temperature is shorter than the elapsed time according to input (step S101). In a case where determination is made that the determined elapsed time at ice temperature is shorter than the elapsed time according to input, the preservation state determination unit 570a determines that the fish has been preserved by freezing, and outputs the determination results thereof (step S102). In a case where determination is made that the determined elapsed time at ice temperature is shorter than the elapsed time according to input, it is also assumed that the determined elapsed time at refrigeration temperature and at room temperature will also be shorter than the elapsed time according to input. Here, the elapsed time after death regarding preservation at each non-freezing temperature (room temperature, refrigeration temperature, and ice temperature) determined from the image of the fish is shorter than the elapsed time according to input, so determination is made that the fish has been preserved by freezing.

In a case where judgment is made in step S101 that the determined elapsed time at ice temperature is not shorter than the elapsed time according to input, the preservation state determination unit 570a compares the elapsed time at refrigeration temperature determined by the elapsed time determination unit 540a referencing the correlation information B based on the state of the melanophores of the fish, with the elapsed time according to the input acquired from the input unit 560, and judges whether or not the determined elapsed time at refrigeration temperature is shorter than the elapsed time according to input (step S103). In a case where determination is made that the determined elapsed time at refrigeration temperature is shorter than the elapsed time according to input, the preservation state determination unit 570a determines that the fish has been preserved at ice temperature, and outputs the determination results thereof (step S104).

Also, in a case where judgment is made in step S103 that the determined elapsed time at refrigeration temperature is not shorter than the elapsed time according to input, the preservation state determination unit 570a compares the elapsed time at room temperature determined by the elapsed time determination unit 540a referencing the correlation information A based on the state of the melanophores of the fish, with the elapsed time according to the input acquired from the input unit 560, and judges whether or not the determined elapsed time at room temperature is shorter than the elapsed time according to input (step S105). In a case where determination is made that the determined elapsed time at room temperature is shorter than the elapsed time according to input, the preservation state determination unit 570a determines that the fish has been preserved at refrigeration temperature, and outputs the determination results thereof (step S106). On the other hand, in a case where determination is made that the determined elapsed time at room temperature is not shorter than the elapsed time according to input, the preservation state determination unit 570a determines that the fish has been preserved at room temperature, and outputs the determination results thereof (step S107).

Thus, the preservation state determination apparatus 50a can determine the temperature at which the first has been preserved, as determination of the state of the fish. The preservation state determination apparatus 50a can also determine whether or not the fish has been preserved by freezing. According to the preservation state determination apparatus 50a, the user can know what sort of preservation state the fish has been in.

Description has been made regarding the first modification of the third embodiment that the correlation information A through C is the correlation between the average area of the melanophores and the amount of time elapsed since the death of the fish, for each preservation temperature, stored in the form of tables, and that the melanophore state analysis unit 120b obtains the average area of the melanophores. Alternatively, an arrangement may be made where correlation between the complexity of shape of the melanophores and the amount of time elapsed since the death of the fish, for each preservation state (preservation temperature), stored in the form of tables. In this case, the analysis unit 120 (melanophore state analysis unit 120b) obtains the complexity of the shapes of the melanophores. The correlation information A may be decided based on experimentation results where the complexity of the shape of melanophores in the fish and the amount of time elapsed since death at room temperature is obtained from multiple fish. The correlation information B may be decided based on experimentation results where the complexity of the shape of melanophores in the fish and the amount of time elapsed since death at refrigeration temperature is obtained from multiple fish. The correlation information C may be decided based on experimentation results where the complexity of the shape of melanophores in the fish and the amount of time elapsed since death at ice temperature is obtained from multiple fish.

Figure 27:
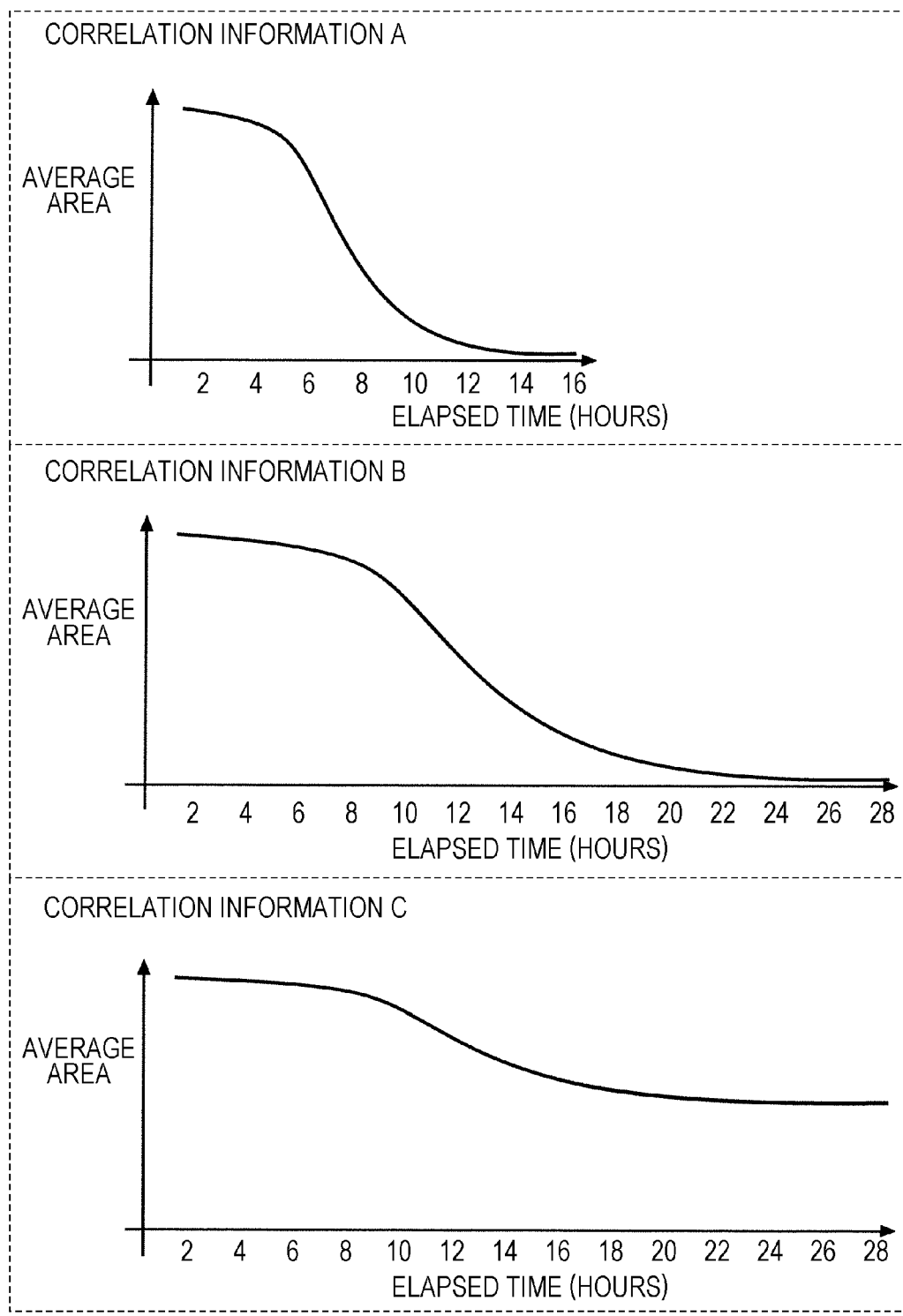
FIG. 27 is a diagram exemplarily illustrating three sets of correlation information (function graphs) according the first modification of the third embodiment.

Moreover, the correlation information representing the correlation between the average area or complexity of shape of the melanophores and the amount of time elapsed since the death of the fish, for each preservation state, is not restricted to being represented in the form of tables, an instead may be expressed as functions or the like. FIG. 27 is a diagram illustrating an example where correlation information A through C is defined as functions representing the correlation between the average area of the melanophores and the amount of time elapsed, for each preservation state. The graphs in FIG. 27 exemplarity illustrate functions representing the correlation between the average area of the melanophores and the amount of time elapsed since the death of the fish that has been obtained by experimentation (functions approximating the correlation, etc.). The correlation information A may be decided based on experimentation results where the average area of melanophores in the fish and the amount of time elapsed since death at room temperature is obtained from multiple fish. The correlation information B may be decided based on experimentation results where the average area of melanophores in the fish and the amount of time elapsed since death at refrigeration temperature is obtained from multiple fish. The correlation information C may be decided based on experimentation results where the average area of melanophores in the fish and the amount of time elapsed since death at ice temperature is obtained from multiple fish.

Second Modification of Third Embodiment

A preservation state determination apparatus 50 that determines the preservation state of a fish, regarding whether the fish has been preserved by freezing at one point or not, by determining the amount of time elapsed since the death of the fish and comparing with the elapsed time after death according to the input, based on the state of the melanophores of the fish, has been illustrated in the third embodiment. In contrast with this, description will be made in a second modification of the third embodiment regarding a preservation state determination apparatus 60 that determines the preservation state of a fish, regarding whether or not the fish has been promptly frozen after landing, without necessitating input of time elapsed since death.

This preservation state determination apparatus 60 has the same hardware configuration as the preservation state determination apparatus 50 according to the third embodiment, but the control program executed by the processor is different, and accordingly the functions differ.

Figure 28:
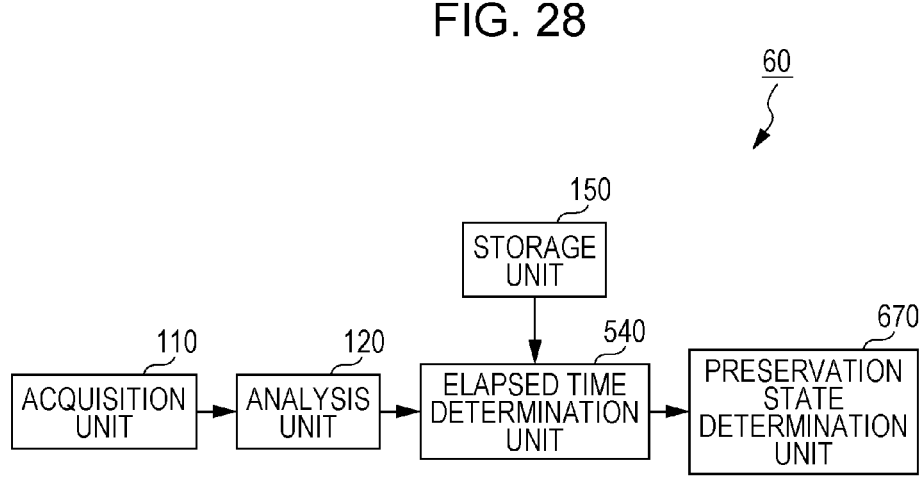
FIG. 28 is a functional block diagram illustrating the configuration of a preservation state determination apparatus according to a second modification of the third embodiment.

FIG. 28 is a functional block diagram illustrating the configuration of the preservation state determination apparatus 60 according to the second modification of the third embodiment. The preservation state determination apparatus 60 functionally includes the acquisition unit 110, the analysis unit 120, the elapsed time determination unit 540, the storage unit 150, and a preservation state determination unit 670, as illustrated in FIG. 28. Note that functional components (functional blocks) the same as those of the preservation state determination apparatus 50 illustrated in the third embodiment are denoted by the same reference numerals, and detailed description will be omitted here. The preservation state determination unit 670 is a partial modification of the preservation state determination unit 570 in the third embodiment.

In the present embodiment, the acquisition unit 110 images an image including a part of the iris of the eye of a fish immediately after thawing. The preservation state determination unit 670 determines the preservation state of the fish using the determination results of the elapsed time determination unit 540, more specifically, whether or not the fish was frozen immediately after landing or a long amount of time was required before freezing, and outputs the determination results.

Figure 29A:
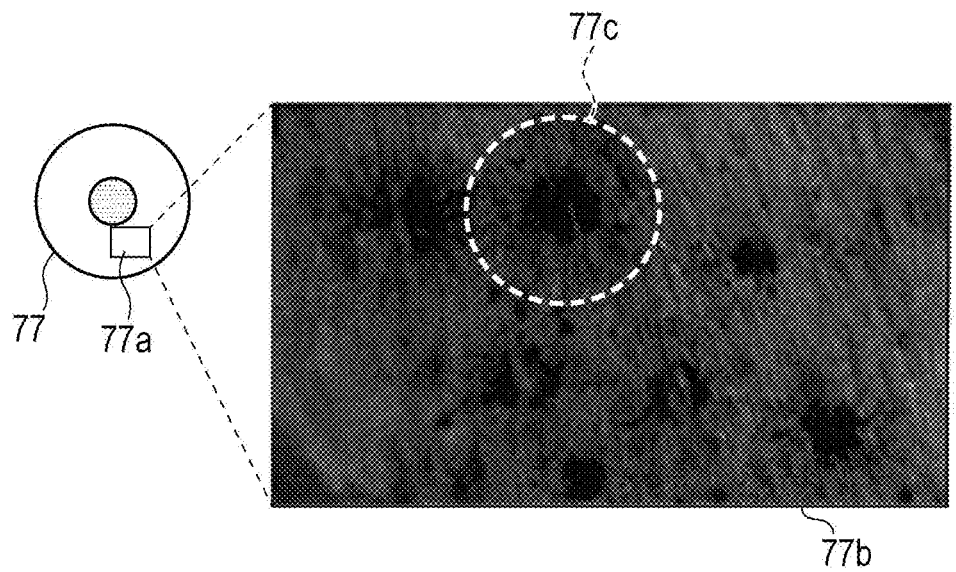
FIG. 29A is a diagram illustrating images of an iris of a fish.
Figure 29B:
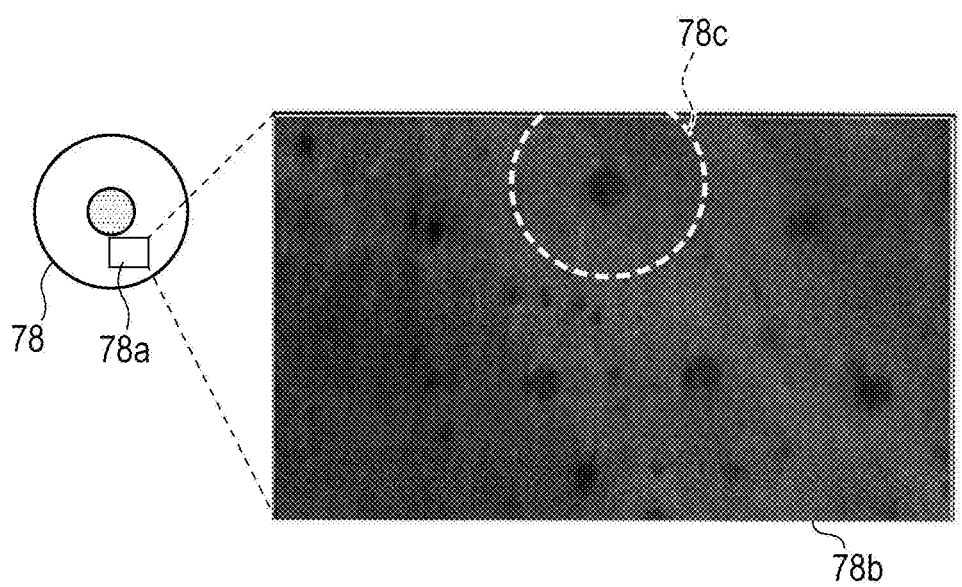
FIG. 29B is a diagram illustrating images of an iris of a fish.

FIG. 29A is a diagram illustrating an image 77b including melanophores of an iris 77a of a fish eye 77 of a fish that was preserved by freezing immediately after landing, photographed immediately after thawing the fish. FIG. 293 is also a diagram illustrating an image 78b including melanophores of an iris 78a of a fish eye 78 of a fish that was preserved by freezing eight hours after landing, photographed immediately after thawing the fish. While the black portion of the melanophore encircled by the circle 77c in image 77b in FIG. 29A has a fairly large area, the black portion of the melanophore encircled by the circle 78c in image 78b in FIG. 29B is small in area, and has become milky in appearance and the luminance is higher. These images are images where a part of the iris 77a and iris 78a has been enlarged 200 times and photographed. As described earlier, the iris region of a fish frozen with little time standing at room temperature has a large black portion of the melanophore even after thawing. In the other hand, if time is allowed to pass before freezing, the area of the black portion of the melanophore after thawing is small, as illustrated in FIG. 29B.

Information representing the correlation between information of melanophores of the multiple sample fish and the amount or time elapsed from landing of the multiple sample fish to preservation by freezing may be held in the storage unit 150 as correlation information. This correlation information may be decided based on experimentation results on information of melanophores of sample fish, i.e., on multiple fish regarding the state of melanophores of the sample fish (e.g., the average area of melanophores or complexity of shape of the melanophores) and elapsed time from landing to preservation by freezing.

The preservation state determination unit 670 may reference the correlation information and determine that the longer the elapsed time determined by the elapsed time determination unit 540 is, the longer amount of time elapsed from landing to freezing. Specifically, a threshold is set, and if the elapsed time determined by the elapsed time determination unit 540 is below the threshold (e.g., 4 hours), determination is made that freezing was performed immediately after landing or within a relatively short time. If the elapsed time determined by the elapsed time determination unit 540 is at or above the threshold (e.g., 4 hours), determination is made that a relatively long amount of time was required to complete freezing preservation after landing. The relationship between elapsed time determined by the elapsed time determination unit 540 and the elapsed time from landing to completion of preservation by freezing may be determined beforehand by experimentation, thus enabling the preservation state determination unit 670 to determine the amount of time required from landing to completion of preservation by freezing, based on the elapsed time determined by the elapsed time determination unit 540.

Figure 30:
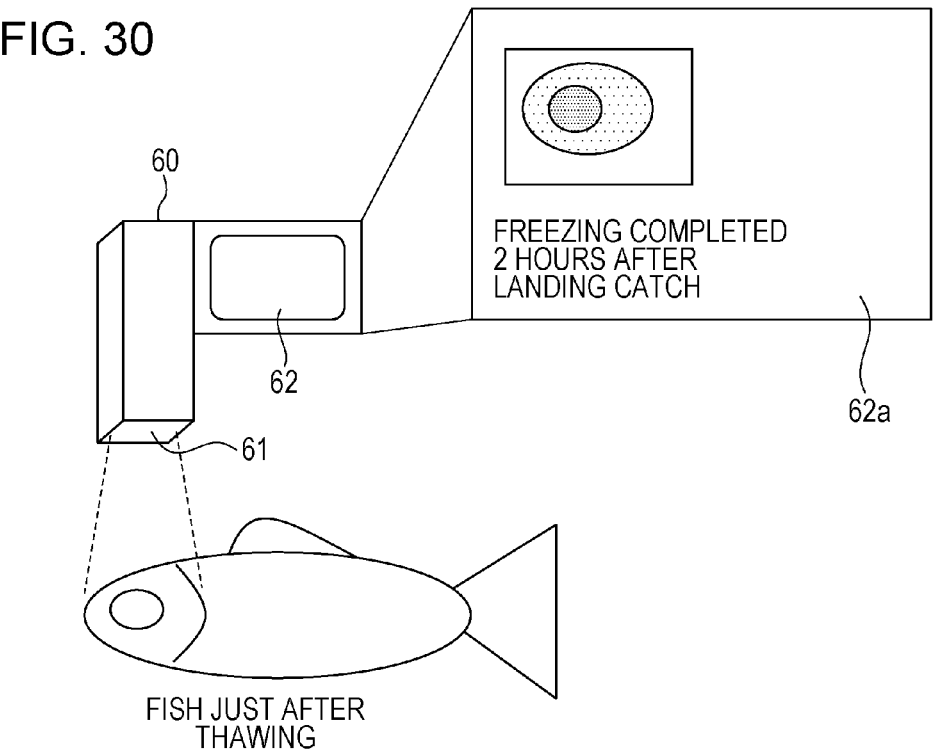
FIG. 30 is a diagram exemplarily illustrating a usage state of the preservation state determination apparatus according to the second modification of the third embodiment.

FIG. 30 is a diagram exemplarily illustrating a usage state of the preservation state determination apparatus 60. The preservation state determination apparatus 60 acquires a photographed image of the iris of the fish immediately after thawing, using an image acquisition unit 61, and outputs (displays) the determination result of the preservation state at an output unit 62 (a display in this example), as illustrated in FIG. 30. The output unit 62 displays an image 62a indicating the determination results that freezing has been completed two hours after landing, for example. Thus, the user can recognize what sort of state the fish was preserved in after being landed, and can select a suitable way to prepare the fish for consumption, or the like, depending on the state of preservation. Setting the binarization threshold for the analysis unit 120 within the range of luminance change of the melanophores results in not only the shape and size of the black portions of the melanophores changing, but also the area of the black portions becoming smaller due to the black portions becoming milky in appearance and the luminance thereof increasing. Thus change over time is accentuated, and accuracy of determination can be improved.

Third Modification of Third Embodiment

The third embodiment has been described as determining the preservation state of a single fish. However, even if multiple fish are preserved in the same freezer or the like, there will be variance in the freezing due to how the cold air flows, resulting in places where it takes time to freeze and places where flash freezing is realized. Description will be made in the present embodiment regarding a modified preservation state determination apparatus which determines what sort of capabilities a freezing apparatus (freezer or the like) which has been used to preserve a fish has, by determining the preservation state of multiple fish preserved in the freezer or the like. This modified preservation state determination apparatus is a partial modification of the preservation state determination apparatus 60 illustrated in the second modification of the third embodiment, as described below.

Figure 31:
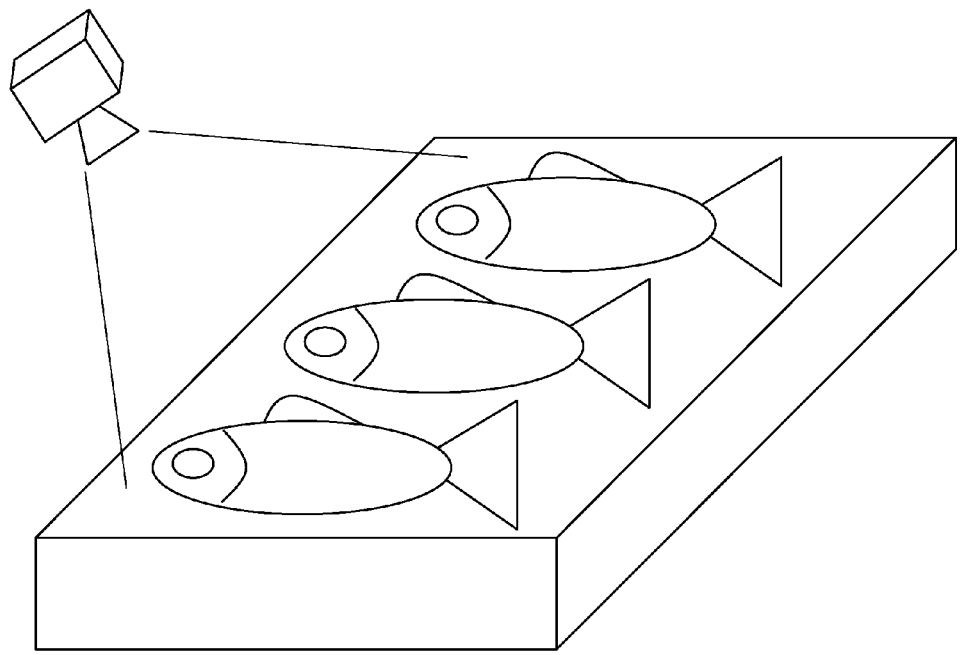
FIG. 31 is a diagram illustrating the way in which multiple fish are photographed by a preservation state determination apparatus according to a third modification of the third embodiment.

The acquisition unit 110 acquires an image which has been generated by photographing multiple fish arrayed in a tray, frozen at the same time by the freezing apparatus, as illustrated in FIG. 31. That is to say, the acquisition unit 110 acquires an image generated by photographing, at the same time, multiple fish frozen at the same time by the freezing apparatus. The analysis unit 120 and elapsed time determination unit 540 determine the amount of time elapsed since the death of each fish by analyzing the state of the melanophores in the irises or fins of each fish in the image. The preservation state determination unit 570 then determines what sort of freezing capabilities the freezing apparatus which has been used to preserve the multiple fish has, based on the distribution of the amount of time elapsed since the death of the multiple fish, determined by the elapsed time determination unit 540. Specifically, in a case where the amount of time elapsed since the death of the multiple fish does not agree, for example, determination is made that the fish have been preserved by a freezing apparatus that has variance in freezing capabilities depending on the position therein. Determination can also be made regarding what position is not being frozen rapidly, and so forth, according to the freezing capabilities, by obtaining position information of each fish and checking the relationship between the distribution of time elapsed after death and the position. Information of the position of each fish may be obtained from the image acquired by the acquisition unit 110, or may be input by the user or any other method.

Figure 32:
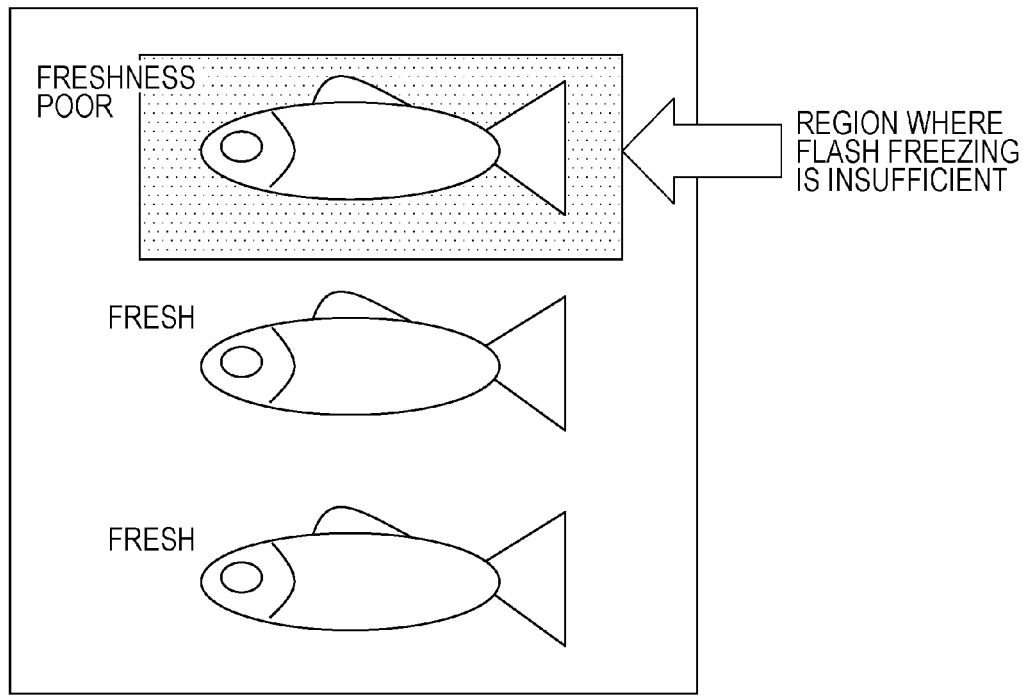
FIG. 32 is a conceptual diagram illustrating determination of freezing capabilities by the preservation state determination apparatus according to the third modification of the third embodiment.

FIG. 32 is a conceptual diagram illustrating determining whether or not each fish is being rapidly frozen, at each position. The freshness of fish, regarding which determination has been made by the elapsed time determination unit 540 that the amount of time elapsed since death is relatively longer than the other multiple fish, is determined to be lower than that of the other fish, and the position where that less-fresh fish was situated is determined to be a position where rapid freezing is not being performed.

Note that photographing may be performed by light reflecting at a predetermined depth from the surface of the fish where the melanophores are present as described in the first embodiment, in each of the first modification and second modification of the first embodiment, the second embodiment, the third embodiment, and the first through third modifications of the third embodiment. Photographing may also be performed at a resolution higher than the resolution of 2 μm per pixel, to analyze the shapes of the melanophores.

Other Embodiments

While elapsed-time determination apparatuses and preservation state determination apparatuses have been described by way of the above embodiments and modifications, the above-described embodiments and modifications are only exemplary, and it is needless to say that various alterations, additions, omissions, and so forth, may be made.

The image acquired by the acquisition unit 110 in the above embodiments may be an image including a part of an iris, an image including a part of a fin, or an image including a portion of another part of the fish including melanophores that change state in the same way as with the iris and fin. It should be noted, however, that images including a part of an iris or fin are suitable for determining the amount of time elapsed since the death of the fish or the preservation state.

Part of the elapsed-time determination method which the elapsed-time determination apparatuses illustrated in the above embodiments executed by the elapsed-time determination processing may also be performed with an external apparatus (computer, etc.) communicable with the elapsed-time determination apparatus. Also, part of the preservation state determination method which the preservation state determination apparatuses illustrated in the above embodiments executed by the preservation state determination processing may be performed with an external apparatus (computer, etc.) communicable with the preservation state determination apparatus.

It should also be noted that the order of execution of the procedures in the elapsed-time determination processing at the elapsed-time determination apparatuses and preservation state determination processing at the preservation state determination apparatuses (procedures illustrated in FIGS. 4, 13, 16, 19, 22, and 25, etc.) is not necessarily restricted to the above-described order; the order of execution may be interchanged, processed in parallel, or partially omitted, without departing from the essence of the disclosure. For example, in FIG. 13, steps S34 and S35, and steps S36 through S38, may be processed in parallel. In FIG. 22, steps S1 through S4 and S6 may be processed in parallel. In FIG. 25, step S541, S542, and S543 may be processed in parallel.

Part or all of the procedures of the elapsed-time determination processing and preservation state determination processing described above may be realized by hardware or may be realized by software. Processing by software is relied by a control processing unit (CPU) included in the elapsed-time determination apparatus, preservation state determination apparatus, etc., executing a control program stored in memory. The program may be recorded in a recording medium and distributed or circulated. For example, part or all of the elapsed-time determination processing and preservation state determination processing may be realized by an apparatus (computer or the like) installing the distributed control program in the apparatus, and causing the CPU of the apparatus to execute the program.

Also, forms realized by optionally combining the components and functions illustrated in the above-described embodiments are also included in the scope of the present disclosure. For example, any of the analysis unit 120, elapsed time determination unit 540, and storage unit 150 in the third embodiment and the modifications thereof may be replaced by the corresponding analysis units, determination units, and storage units illustrated in the first embodiment and modifications thereof and the second embodiment. The determined amount of time elapsed since the death of the fish to be transmitted to the preservation state determination unit in the third embodiment and modifications thereof may be that determined by the methods illustrated in the first embodiment and modifications thereof and the second embodiment.

The determination unit 140 handling the determination and output in the above-described elapsed-time determination apparatus may be replaced by an output unit that outputs information representing the amount of time elapsed since the death of the fish determined following that correlation, based on the above-described correlation information representing a certain correlation, according to the state of the melanophores of the fish detected by the analysis unit 120. This elapsed-time determination apparatus after the replacement is an elapsed-time information output apparatus, so as to say. Also, the elapsed time determination unit 540 handling determination and the preservation state determination unit 570 handling determination and output in the above-described elapsed-time determination apparatus may be replaced with an output unit that outputs information indicating whether the fish has been in a frozen state at one point, based on the relationship between the amount of time elapsed since the death of the fish in a non-frozen state determined based on the above-described correlation information representing a certain correlation, according to the state of the melanophores of the fish detected by the analysis unit 120, and the elapsed time accepted by the input unit 560 (e.g., step S7 in FIG. 22). This preservation state determination apparatus after the replacement is a preservation state information output apparatus, so as to say. Note that examples of output of information by the output units include display of information on a display device such as a display, output of information by audio, output of information by printing, transmission of information to an external apparatus, and so forth.

Figure 33:
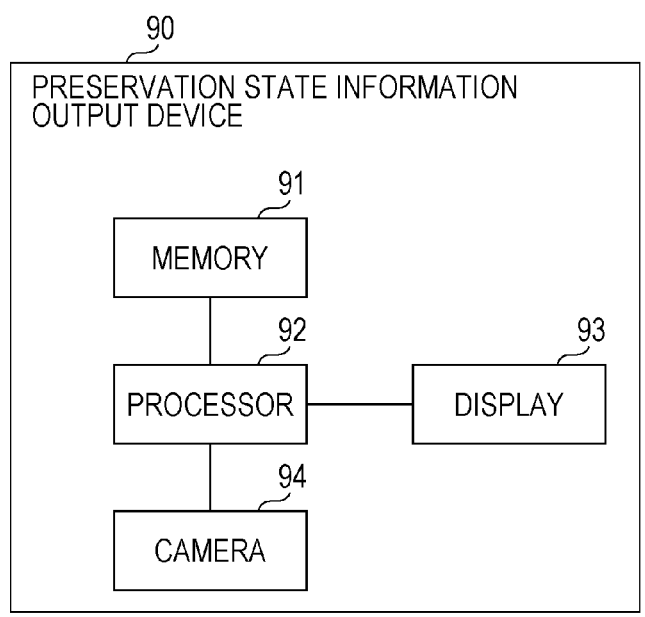
FIG. 33 is a configuration diagram of a preservation state information output device according to another embodiment.

A specific form of the preservation state determination apparatus described above is a preservation state determination apparatus 90, of which the configuration is illustrated in FIG. 33, that displays the preservation state of fish based on the above-described correlation information. The preservation state determination apparatus 90 includes memory 91, a processor 92, a display 93, and a camera 94. The memory 91 stores correlation information representing the correlation between the state of the melanophores of the fish, and the amount of time elapsed since the death of the fish in a case of the fish not being frozen (e.g., the correlation information illustrated in FIG. 8, the correlation information A through C illustrated in FIG. 24 or FIG. 26, and so forth). The processor 92 has the functions of identifying the amount of time elapsed since the death of the fish in a case of the fish not being frozen based on the correlation information in the memory 91, in accordance with the state of the melanophores appearing in the image of the fish that has been input, identifying the preservation state of the fish in accordance with the identified elapsed time, and outputting preservation state information representing the identified preservation state.

The processor 92 exhibits these functions by executing a program stored in memory, for example. The display 93 displays preservation state information output from the processor 92. The camera 94 photographs images of fish, and inputs the images to the processor 92. The preservation state determination apparatus 90 may include a receipt circuit or the like that externally receives images of fish and inputs to the processor 92, instead of the camera 94. Note that identifying the preservation state of the fish at the processor 92 is performed by the amount of time elapsed since the death of the fish identified based on the correlation information in the memory 91 in accordance with the image being compared with a predetermined elapsed time or an input elapsed time (e.g., performed by procedures in step S8, steps S101 through S107, and so forth).

The present disclosure is applicable to an apparatus that determines the amount of time elapsed since the death of the fish or the preservation state thereof.

What is claimed is:

1. An elapsed-time determination apparatus comprising:
   a non-transitory computer-readable storage medium that stores correlation information indicating a correlation between a state of a melanophore of a fish and an amount of time elapsed since death of the fish; and
   a processor that executes a control program to cause the elapsed-time determination apparatus to function as:
   an acquisition unit that acquires an image of a fish;
   an analysis unit that detects a state of a melanophore of a fish by analyzing the image acquired by the acquisition unit; and
   a determination unit that determines the amount of time elapsed since the death of the fish in accordance with the state of the melanophore of the fish detected by the analysis unit, based on the correlation information, and outputs determination results,
   wherein the correlation information indicates a correlation where the smaller the size of a black portion of a melanophore is, the longer the elapsed time after death is, and
   wherein the analysis unit detects the size of the black portion of the melanophore as the state of the melanophore of the fish.

2. The elapsed-time determination apparatus according to claim 1,
   wherein the image of the fish acquired by the acquisition unit includes part of an iris or fin of the fish.

3. The elapsed-time determination apparatus according to claim 1,
   wherein the state of the melanophore in the correlation information is indicated in the form of features including the area of the black portion of the melanophore and the degree of complexity of the shape of the black portion, and
   wherein the analysis unit detects the features as the state of the melanophore of the fish.

4. The elapsed-time determination apparatus according to claim 1,
   wherein the image of the fish acquired by the acquisition unit is an image photographed by irradiating the fish with light including an ultraviolet region.

5. An elapsed-time determination apparatus comprising:
   a non-transitory computer-readable storage medium that stores correlation information indicating a correlation between a state of a melanophore of a fish and an amount of time elapsed since death of the fish; and a processor that executes a control program to cause the elapsed-time determination apparatus to function as:

an acquisition unit that acquires an image of a fish;

an analysis unit that detects a state of a melanophore of a fish by analyzing the image acquired by the acquisition unit; and a determination unit that determines the amount of time elapsed since the death of the fish in accordance with the state of the melanophore of the fish detected by the analysis unit, based on the correlation information, and outputs determination results, wherein the correlation information indicates a correlation where the lower the degree of complexity of the shape of a black portion of a melanophore is, the longer the elapsed time after death is, and wherein the analysis unit detects the degree of complexity of the shape of the black portion of the melanophore as the state of the melanophore of the fish.

6. The elapsed-time determination apparatus according to claim 5, wherein the image of the fish acquired by the acquisition unit includes part of an iris or fin of the fish.

7. The elapsed-time determination apparatus according to claim 5, wherein the state of the melanophore in the correlation information is indicated in the form of features including the area of the black portion of the melanophore and the degree of complexity of the shape of the black portion, and wherein the analysis unit detects the features as the state of the melanophore of the fish.

8. The elapsed-time determination apparatus according to claim 5, wherein the image of the fish acquired by the acquisition unit is an image photographed by irradiating the fish with light including an ultraviolet region.

9. The elapsed-time determination apparatus according to claim 5, wherein the degree of complexity is decided based on the perimeter of the black portion, and wherein the shorter the perimeter of the black portion is, the longer the elapsed time is.

* * * * *